United States Patent [19]

Hagmann et al.

[11] Patent Number: 5,403,952

[45] Date of Patent: Apr. 4, 1995

[54] SUBSTITUTED CYCLIC DERIVATIVES AS NOVEL ANTIDEGENERATIVE AGENTS

[75] Inventors: William Hagmann, Westfield; Charles G. Caldwell, Scotch Plains; Paul R. Gooley, Westfield, all of N.J.

[73] Assignee: Merck & Co., Inc., Rahway, N.J.

[21] Appl. No.: 133,493

[22] Filed: Oct. 8, 1993

[51] Int. Cl.⁶ ............................................. C07K 7/100
[52] U.S. Cl. ............................... 510/85; 560/10;
560/15; 560/18; 560/24; 560/25; 560/26;
560/34; 560/51; 560/53; 560/54; 560/55;
560/56; 560/60; 560/76; 560/80; 560/100;
562/433; 562/439; 562/459; 562/461; 562/470;
562/473; 562/488; 562/490
[58] Field of Search ............... 560/85, 10, 15, 18,
560/24, 25, 26, 34, 51, 53, 54, 55, 56, 60, 76, 80,
100, 122; 562/433, 439, 459, 461, 470, 473, 488,
490; 514/530, 561, 562, 564, 565

[56] References Cited

U.S. PATENT DOCUMENTS 4,256,108  3/1981  Theeuwes ........................ 560/20
4,265,874  5/1981  Bonsen et al. .................. 560/20

FOREIGN PATENT DOCUMENTS 0337549  10/1989  European Pat. Off. ........... 560/19
92/21360  10/1992  WIPO ................................ 560/19
93/14112   2/1993  WIPO ................................ 560/19

OTHER PUBLICATIONS

Richardson, P. D. et al. The Lancet, Oct. 21, 1989 pp. 941–944.
Blanckaert, A. et al. Clinica Chimica Acta, 185 (1989) pp. 73–80.
Steroids, 54/5, Nov. 1989, pp. 491–499, by J. Woessner, Jr., et al.
Genes & Development 3:848–859, 1989, by C. Brenner, et al.
Biochemical and Biophysical Research Communication, vol. 174, No. 2, 1991, pp. 1003–1008, by D. Sawamura, et al.
Proc. Natl. Acad. Sci., vol. 88, pp. 8154–8158, Sep. 1991, Med. Sciences, by A. Henney, et al.
FEBS 09372, vol. 279, No. 1, pp. 91–94, by Winyard, et al. Dec. 7, 1990.
Proc. Natl. Acad. Sci. USA, vol. 83, pp. 9413–9417, Dec. 1986, Biochem., by L. Matrisian, et al.
1988 Metastasis. Wiley, Chichester (Ciba Found. Symposium 141) pp. 193–210, by R. Reich, et al.

(List continued on next page.)

*Primary Examiner*—Marianne M. Cintins
*Assistant Examiner*—Keith MacMillan
*Attorney, Agent, or Firm*—Curtis C. Panzer; David L. Rose; Robert J. North

[57] ABSTRACT

Novel substituted cyclic compounds of Formula I are found to be useful inhibitors of matrix metalloendoproteinase-mediated diseases including osteoarthritis, rheumatoid arthritis, septic arthritis, tumor invasion in certain cancers, periodontal disease, corneal ulceration, proteinuria, dystrophic epidermolysis bullosa, and coronary thrombosis associated with atherosclerotic plaque rupture. The matrix metalloendoproteinases are a family of zinc-containing proteinases including but not limited to stromelysin, collagenase, and gelatinase, that are capable of degrading the major components of articular cartilage and basement membranes. The inhibitors claimed herein may also be useful in preventing the pathological sequelae following a traumatic injury that could lead to a permanent disability. These compounds may also be useful as novel birth control agents by preventing ovulation or implantation.

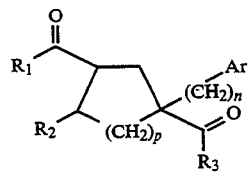

13 Claims, No Drawings

OTHER PUBLICATIONS

J. of Cell Biology, vol. 109, Aug. 1989, pp. 877–889, by Z. Werb, et al.

J. of Clin. Investigation, Inc., vol. 84, Dec. 1989, pp. 1731–1740, by J. Case, et al.

Fur. J. Biochem. vol. 194, pp. 721–730 (1990) by Y. Okada, et al.

Biochem. & Biophys. Research Comm., vol. 133, No. 2, 1985, pp. 483–490, by J. Delaisse.

Progress in Medicinal Chem., vol. 29, 1992, pp. 271–344, by M. Schwartz, et al.

Biochem. J (1986) 240, pp. 913–916, by S. Whitham, et al.

J. Enzyme Inhib. 1987, vol. 2, pp. 1–22, by W. Johnson, et al.

Advances in Inflammation Research, vol. 12, 1988, pp. 67–79, by A. Shaw, et al.

Archives of Biochem. & Biophysics, vol. 267, No. 1, 1988, pp. 211–216, by A. Ito, et al.

Biochem. J (1987) vol. 248, pp. 265–268, by G. Murphy, et al.

J. of Biological Chemistry, vol. 267, No. 6, 1992, pp. 3581–3584, by Y. Ogata, et al.

Biochem. and Biophysical Research Comm., vol. 185, No. 3, 1992, pp. 852–859, by K. Miyazaki, et al.

Amer. J. of Pathology, vol. 142, No. 1. Jan. 1993, vy J. Pelletier, et al.

Strangeways Research Lab. 75th Anniv. Symposium, Apr. 6–8, 1987, Elsevier, Chapter 14, pp. 179–195, by S. M. Krane, et al.

Clinica Chimica Acta. 185 (1989) pp. 73–80, Elsevier, by A. Blanckaert, et al.

Arthritis and Rheumatism, vol. 33, No. 3 (Mar. 1990), by K. Hasty, et al.

Investigative Ophthalkmology & Visual Science, vol. 30, No. 7, Jul. 1989, pp. 1569–1575, by F. R. Burns, et al.

J. of Biol. Chem., vol. 264, No. 8, Mar. 15, pp. 4277–4281, 1989, by M. Stack.

Biochem. J. (1988) vol. 254, pp. 609–612, by W. Baricos, et al.

Biochem. (1988), vol. 31, pp. 12618–12623, by L. Niedzwiecki, et al.

J. of Periodontal Research, 1987, vol. 22, pp. 81–88, by C. Overall, et al.

J. of Periodontal Research, 1981, vol. 16, pp. 417–424, by V. Uitto, et al.

Analytical Biochem., vol. 180, pp. 110–113, 1989, by R. Harrison, et al.

JACS, vol. 70, Jun. 1948, pp. 2209–2215, by L. Smith, et al.

Arthritis and Rheumatism, vol. 35, No. 1 (Jan. 1992), pp. 25–42, by L. Walakowits, et al.

Endocrinology, vol. 115, No. 3, 1984, by C. Too, et al.

Arch Ophthal, vol. 81, Mar. 1969, pp. 370–373, by S. Brown, et al.

Lab. Investigation, vol. 49, No. 6 (1983), pp. 636–649, by L. Liotta, et al.

J. of Orthopaedic Research, vol. 6, pp. 103–108, 1988, by C. Caputo, et al.

J. of Orthopaedic Research, 9:259–265, 1991, by R. Williams, et al.

Proc. Natl. Acad. Sci. USA, vol. 84, pp. 6725–6729 (Oct. 1987), Biochemistry, by S. Wihelm, et al.

SUBSTITUTED CYCLIC DERIVATIVES AS NOVEL ANTIDEGENERATIVE AGENTS

BACKGROUND OF THE INVENTION

1. Field of the Invention

By this invention there is provided novel substituted cyclic compounds of Formula I which are useful inhibitors of matrix metalloendoproteinase-mediated diseases including osteoarthritis, rheumatoid arthritis, septic arthritis, tumor invasion in certain cancers, periodontal disease, corneal ulceration, proteinuria, dystrophic epidermolysis bullosa, and coronary thrombosis associated with atherosclerotic plaque rupture. The matrix metalloendoproteinases are a family of zinc-containing proteinases including but not limited to stromelysin, collagenase, and gelatinase, that are capable of degrading the major components of articular cartilage and basement membranes. The inhibitors claimed herein may also be useful in preventing the pathological sequelae following a traumatic injury that could lead to a permanent disability. These compounds may also be useful as novel birth control agents by preventing ovulation or implantation.

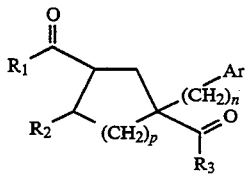

I

2. Brief Description of Disclosures in the Art

The disability observed in osteoarthritis (OA) and rheumatoid arthritis (RA) is largely due to the loss of articular cartilage. No therapeutic agent in the prior art is known to prevent the attrition of articular cartilage in these diseases.

"Disease modifying antirheumatic drugs" (DMARD), i.e., agents capable of preventing or slowing the ultimate loss of joint function in OA and RA are widely sought. Generic nonsteroidal antiinflammatory drugs (NSAIDs) may be combined with such agents to provide some relief from pain and swelling.

Stromelysin (aka. proteoglycanase, matrix metalloproteinase-3, MMP-3, procollagenase activator, "transin"), collagenase (aka. interstitial collagenase, matrix metalloproteinase-1), and gelatinase (aka. type IV collagenase, matrix metalloproteinase-2, MMP-2, 72kDa-gelatinase, gelatinase A or type V collagenase, matrix metalloproteinase-9, MMP-9, 95kDagelatinase, gelatinase B) are metalloendoproteinases secreted by fibroblasts, chondrocytes, and macrophage and are capable of degrading the major connective tissue components of articular cartilage or basement membranes. Elevated levels of these enzymes have been detected in joints of arthritic humans and animals: K. A. Hasty, R. A. Reife, A. H. Kang, J. M. Smart, "The role of stromelysin in the cartilage destruction that accompanies inflammatory arthritis", Arthr. Rheum., 33, 388–97 (1990); S. M. Krane, E. P. Amento, M. B. Goldting, S. R. Goldring, and M. L. Stephenson, "Modulation of matrix synthesis and degradation in joint inflammation", in "The Control of Tissue Damage", A. B. Glauert (ed.), Elsevier Sci. Publ., Amsterdam, 1988, Ch. 14, pp 179–95; A. Blanckaert, B. Mazieres, Y. Eeckhout, G. Vaes, "Direct extraction and assay of collagenase from human osteoarthrtic cartilage", Clin. Chem. Acta, 185 73–80 (1989); J.-P. Pelletier, M.-P. Faure, J. A. DiBattista, S. Wilhelm, D. Visco, J. Martel-Pelletier, "Coordinate Synthesis of Stromelysin, Interleukin-1, and Oncogene Proteins in Experimental Osteoarthritis", Am. J. Path. 142, 95–105 (1993); L. A. Walakovits, N. Bhardwaj, G. S. Gallick, M. W. Lark, "Detection of high levels of stromelysin and collagenase in synovial fluid from patients with rheumatoid arthritis and post-traumatic knee injury", Arthr. Rheum. 35, 35–42 (1992). Each enzyme is secreted from these cells as an inactive proenzyme which is subsequently activated. There is evidence that stromelysin may be the in vivo activator for collagenase and gelatinase, implying a cascade for degradative enzyme activity: A. Ho, H. Nagase, "Evidence that human rheumatoid synovial matrix metalloproteinase 3 is an endogenous activator of procollagenase", Arch Biochem Biophys., 267, 211–16 (1988); G. Murphy, M. I. Crockett, P. E. Stephens, B. J. Smith, A. J. P. Docherty, "Stromelysin is an activator of procollagenase", Biochem. J., 248, 265–8 (1987); Y. Ogata, J. J. Enghild, H. Nagase, "Matrix Metalloproteinase 3 (stromelysin) activates the precursor for the human matrix metalloproteinase 9", J. Biol. Chem. 267, 3581–3584 (1992); K. Mikazaki, F. Umenishi, K. Funahashi, N. Yasumitsu, M. Umeda, "Activation of TIMP-2/Progelatinase A Complex by Stromelysin", Biochem. Biophys. Res. Commun., 185, 852–859 (1992). Inhibiting stromelysin could limit the activation of collagenase and gelatinase as well as prevent the degradation of proteoglycan.

That stromelysin inhibition may be effective in preventing articular cartilage degradation has been demonstrated in vitro by measuring the effect of matrix metalloendoproteinase inhibitors on promoglycan release from rabbit cartilage explants: C. B. Caputo, L. A. Sygowski, S. P. Patton, D. J. Wolanin, A. Shaw, R. A. Roberts, G. DiPasquale, J. Orthopaedic Res., 6, 103–8 (1988).

There is an extensive literature on the involvement of these metalloproteinases in arthritis, but there is very little to guide one in developing a specific inhibitor for each enzyme.

In preliminary studies of rabbit proteoglycanase with substrates and inhibitors, little was found to indicate the enzyme's requirements for hydrolysis or inhibition beyond a preference for hydrophobic residues at the $P_{1'}$ position: A. Shaw, R. A. Roberts, D.J. Wolanin, "Small substrates and inhibitors of the metalloproteoglycanase of rabbit articular chondrocytes", Adv. Inflam. Res., 12, 67–79 (1988).

Human rheumatoid synovial collagenase has been shown to share ~50% homology with human stromelysin: S. E. Whitham, G. Murphy, P. Angel, H. J. Rahmsdorf, B. J. Smith, A. Lyons, T. J. R. Harris, J. J. Reynolds, P. Herrlich, A. J. P. Docherty, "Comparison of human stromelysin and collagenase by cloning and sequence analysis", Biochem. J., 240, 913–6 (1986). Many collagenase inhibitors have been designed around the cleavage site of the a-chain sequence of Type II collagen: W. H. Johnson, N. A. Roberts, N. Brokakoti, "Collagenase inhibitors: their design and potential therapeutic use", J. Enzyme Inhib., 2,1–22 (1987); M. A. Schwartz, H. E. Van Wart, "Synthethic Inhibitors of Bacterial and Mammalian Interstitial Collagenases", in Progress in Medicinal Chemistry, vol 29, G. P. Ellis, D. K. Luscombe (eds.), Elsevier Sci. Publish., Amsterdam, 1992, pp 271–334. One such inhibitor, N-[3-(benzyloxycarbonyl)amino-1-carboxy-n-propyl]-L-leucyl-O-methyl-L-tyrosine, N-methylamide, prepared at G. D. Searle, Inc., and shown to be a potent inhibitor of human rheumatoid synovial collagenase ($IC_{50}=0.8$ μM), was also found to inhibit rabbit bone proteoglycanase ($IC_{50}=0.5$ μM): J. -M. Delaisse, Y. Eeckhout, C. Sear, A. Galloway, K. McCullagh, G. Vaes, "A new synthetic inhibitor of mammalian tissue collagenase inhibits bone resorption in culture", *Biochem. Biophys. Res. Commun.*, 133,483–90 (1985).

Gelatinase-A (MR~72,000) has been isolated from rheumatoid fibroblasts: Y. Okada, T. Morodomi, J. J. Enghild, K. Suzuki, A. Yasui, I. Nakanishi, G. Salvesen, H. Nagase, "Matrix metalloproteinase 2 from human rheumatoid synovial fibroblasts", *Eur. J., Biochem.*, 194, 721–30 (1990). The synthesis of the proenzyme of this matrix metalloproteinase is not coordinately regulated with stromelysin or collagenase and its activation may also be different. The role of gelatinase-A in the tissue destruction of articular cartilage appears different from the other two enzymes and, therefore, its inhibition may provide additional protection from degradation. A higher molecular weight gelatinase-B (MR~95,000; aka. type-V collagenase, matrix metalloproteinase-9, MMP-9) is also secreted by fibroblasts and monocytes and may be involved in cartilage degradation.

As appreciated by those of skill in the art, the significant proportion of homology between human fibroblast collagenase, stromelysin, and gelatinase leads to the possibility that a compound that inhibits one enzyme may to some degree inhibit all of them.

The applicants believe that matrix metalloproteinase inhibitors have utility in preventing articular cartilage damage associated with septic arthritis. Bacterial infections of the joints can elicit an inflammatory response that may then be perpetuated beyond what is needed for removal of the infective agent resulting in permanent damage to structural components. Bacterial agents have been used in animal models to elicit an arthritic response with the appearance of proteolytic activities. See J. P. Case, J. Sano, R. Lafyatis, E. F. Remmers, G. K. Kumkumian, R. L. Wilder, "Transin/stromelysin expression in the synovium of rats with experimental erosive arthritis", *J. Clin Invest.*, 84, 1731–40 (1989); R. J. Williams, R. L. Smith, D. J. Schurman, "Septic Arthritis: Staphylococcal induction of chondrocyte proteolytic activity", *Arthr. Rheum.*, 33, 533–41 (1990).

The applicants also believe that inhibitors of stromelysin, collagenase, and gelatinase will be useful to control tumor metastasis, optionally in combination with current chemotherapy and/or radiation. See L. M. Matrisian, G. T. Bowden, P. Krieg, G. Furstenberger, J. P. Briand, P. Leroy, R. Breathnach, "The mRNA coding for the secreted protease transin is expressed more abundantly in malignant than in benign tumors", *Proc. Natl. Acad. Sci., USA*, 83, 9413–7 (1986); S. M. Wilhelm, I. E. Collier, A. Kronberger, A. Z. Eisen, B. L. Mariner, G. A. Grant, E. A. Bauer, G. I. Goldberg, "Human skin fibroblast stromelysin: structure, glycosylation, substrate specificity, and differential expression in normal and tumorigenic cells", *Ibid.*, 84, 6725–29 (1987); Z. Werb et al., Signal transduction through the fibronectin receptor induces collagenase and stromelysin gene expression, *J. Cell Biol.*, 109, 872–889 (1989); L. A. Liotta, C. N. Rao, S. H. Barsky, "Tumor invasion and the extracellular matrix", *Lab. Invest.*, 49, 636–649 (1983); R. Reich, B. Stratford, K. Klein, G. R. Martin, R. A. Mueller, G. C. Fuller, "Inhibitors of collagenase IV and cell adhesion reduce the invasive activity of malignant rumor cells", in "Metastasis: Ciba Foundation Symposium"; Wiley, Chichester, 1988, pp. 193–210.

Secreted proteinases such as stromelysin, collagenase, and gelatinase play an important role in processes involved in the movement of cells during metastasic rumor invasion. Indeed, there is also evidence that the matrix metalloproteinases are overexpressed in certain metastatic minor cell lines. In this context, the enzyme functions to penetrate underlying basement membranes and allow the tumor cell to escape from the site of primary tumor formation and enter circulation. After adhering to blood vessel walls, the tumor cells use these same metalloendoproteinases to pierce underlying basement membranes and penetrate other tissues, thereby leading to tumor metastasis. Inhibition of this process would prevent metastasis and improve the efficacy of current treatments with chemothempeutics and/or radiation.

These inhibitors should also be useful for controlling periodontal diseases, such as gingivitis. Both collagenase and stromelysin activities have been isolated from fibroblasts isolated from inflammed gingiva: V. J. Uitto, R. Applegren, P. J. Robinson, "Collagenase and neutral metalloproteinase activity in extracts of inflamed human gingiva", *J. Periodontal Res.*, 16, 417–424 (1981). Enzyme levels have been correlated to the severity of gum disease: C. M. Overall, O. W. Wiebkin, J. C. Thonard, "Demonstration of tissue collagenase activity in vivo and its relationship to inflammation severity in human gingiva", *J. Periodontal Res.*, 22, 81–88 (1987).

Proteolytic processes have been observed in the ulceration of the cornea following alkali bums: S. I. Brown, C. A. Weller, H. E. Wasserman, "Collagenolytic activity of alkali-bumed corneas", *Arch. Opthalmol.*, 81,370–373 (1969). Mercapto-containing peptides inhibit the collagenase isolated from alkali-burned rabbit comea: F. R. Bums, M. S. Stack, R. D. Gray, C. A. Paterson, *Invest. Opthalmol.*, 30, 1569–1575 (1989). Treatment of alkali-burned eyes or eyes exhibiting comeal ulceration as a result of infection with inhibitors of these metalloendoproteinases in combination with sodium citrate or sodium ascorbate and/or antimicrobials may be effective in preventing developing comeal degradation.

Stromelysin has been implicated in the degradation of structural components of the glomemlar basement membrane (GBM) of the kidney, the major function of which is to restrict passage of plasma proteins into the urine; W. H. Baricos, G. Murphy, Y. Zhou, H. H. Nguyen, S. V. Shah, "Degradation of glomemlar basement membrane by purified mammalian metalloproteinases", *Biochem. J.*, 254, 609–612 (1988). Proteinuria, a result of glomerular disease, is excess protein in the u fine caused by increased permeability of the GBM to plasma proteins. The underlying causes of this increased GBM permeability are unknown, but proteinases including stromelysin may play an important role in glomemlar diseases. Inhibition of this enzyme may alleviate the proteinura associated with kidney malfunction.

It is suggested that inhibition of stromelysin activity may prevent the rapturing of atherosclerotic plaques leading to coronary thrombosis. The tearing or rapture of atherosclerotic plaques is the most common event initiating coronary thrombosis. Destabilization and degradation of the connective tissue matrix surrounding these plaques by proteolytic enzymes or cytokines released by infiltrating inflammatory cells has been proposed as a cause of plaque fissuring. Such tearing of these plaques can cause an acute thrombolytic event as blood rapidly flows out of the blood vessel. High levels of stromelysin RNA message have been found to be localized to individual cells in atherosclerotic plaques removed from heart transplant patients at the time of surgery: A. M. Henney, P. R. Wakeley, M. J. Davies, K. Foster, R. Hembry, G. Murphy, S. Humphdes, "Localization of stromelysin gene expression in atherosclerotic plaques by in situ hybridization", *Proc. Nat'l. Acad. Sci. USA*, 88, 8154–8158 (1991). Inhibition of stromelysin by these compounds may aid in preventing or delaying the degradation of the connective tissue matrix that stabilizes the atherosclerotic plaques, thereby preventing events leading to acute coronary thrombosis.

Collagenolytic and stromelysin activity have also been observed in dystrophic epidermolysis bullosa: A. Kronberger, K. J. Valle, A. Z. Eisen, E. A. Bauer, *J. Invest. Dermatol.*, 79 208–211 (1982); D. Sawamura, T. Sugawara, I. Hashimoto, L. Bruckmer-Tuderman, D. Fujimoto, Y. Okada, N. Utsumi, H. Shikata, *Biochem. Biophys. Res. Commun.*, 174, 1003–8 (1991). Inhibition of metalloendoproteinases should limit the rapid destruction of connective components of the skin.

It is also believed that specific inhibitors of stromelysin and collagenase should be useful as birth control agents. There is evidence that expression of metalloendoproteinases, including stromelysin and collagenase, is observed in unfertilized eggs and zygotes and at further cleavage stages and increased at the blastocyst stage of fetal development and with endoderm differentiation: C. A. Brenner, R. R. Adler, D. A. Rappolee, R. A. Pedersen, Z. Werb, "Genes for extracellular matrix-degrading metalloproteinases and their inhibitor, TIMP, are expressed during early mammalian development", *Genes & Develop.*, 3, 848–59 (1989). By analogy to tumor invasion, a blastocyst may express metalloproteinases in order to penetrate the extracellular matrix of the uterine wall during implantation. Inhibition of stromelysin and collagenase during these early developmental processes should presumably prevent normal embryonic development and/or implantation in the uterus. Such intervention would constitute a novel method of birth control. In addition there is evidence that collagenase is important in ovulation processes. In this example, a covering of collagen over the apical region of the follicle must be penetrated in order for the ovum to escape. Collagenase has been detected during this process and an inhibitor has been shown to be effective in preventing ovulation: J. F. Woessner, N. Morioka, C. Zhu, T. Mukaida, T. Butler, W. J. LeMaire "Connective tissue breakdown in ovulation", *Steroids*, 54, 491–499 (1989). There may also be a role for stromelysin activity during ovulation: C. K. L. Too, G. D. Bryant-Greenwood, F. C. Greenwood, "Relaxin increases the release of plasminogen activator, collagenase, and proteo-glycanase from rat granulosa cells in vitro", *Endocrin.*, 115, 1043–1050 (1984).

Metalloendoproteinases have also been implicated in the cleavage of proteins associated with the myelin sheath surrounding nerve fibers: A. Chantry, C. Earl, N. Groome, P. Glynn, "Metalloendoprotease Cleavage of 18.2- and 14.1-kilodalton basic proteins dissociating from rodent myelin membranes generates 10.0and 5.9kilodalton C-terminal fragments", *J. Neurochem.* 50, 688–694 (1988). Inhibitors of such processes may prevent nerve sheath degeneration associated with several neurological diseases, including muscular dystrophy.

In addition to extracellular matrix comprising structural components, stromelysin can degrade other in vivo substrates including the inhibitors a I-proteinase inhibitor and may therefore influence the activities of other proteinases such as elastase: P. G. Winyard, Z. Zhang, K. Chidwick, D. R. Blake, R. W. Carrell, G. Murphy, "Proteolytic inactivation of human a$_1$-antitrypsin by human stromelysin", *FEBS Letts.*, 279, 1, 91–94 (1991 ). Inhibition of the matrix metalloendoproteinases may potentiate the antiproteinase activity of these endogenous inhibitors.

SUMMARY OF THE INVENTION

By this invention there is provided a class of novel substituted cyclic compounds of the following Formula I which are useful inhibitors of matrix metalloendoproteinase-mediated diseases including degenerative diseases (such as defined above) and certain cancers:

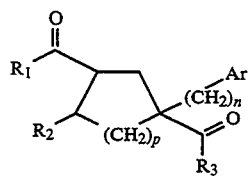

wherein:

n is 1–4;

p is 1–2;

Ar is an aryl or heteroaryl group selected from the group consisting of:
(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carboxazolyl,
(23) isoxazolyl,
(24) thiazolyl,
(25) oxazolyl,
(26) benzthiazolyl, and
(27) benzoxazolyl, which can be mono- or di-substituted with substituents independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, $C_{1-6}$alkylcarbonyl, aryl or heteroaryl as defined above;

$R_1$ is NHOH, OH, O$C_{1-10}$alkyl, OCH($C_{1-10}$alkyl)OC-(O)$C_{1-10}$alkyl, OCH$_2$phenyl, wherein the phenyl group may be substituted with hydrogen, carboxy, carboxy$C_{1-3}$alkyl, aminocarbonyl, $C_{1-6}$ alkylaminocarbonyl; R 2 is hydrogen or a mono- or di-substituted C$_{1-6}$alkyl, C$_{1-6}$alkoxy, or C$_{2-6}$alkenyl wherein the substituents are independently selected from the group consisting of:
(a) hydrogen,
(b) carboxy,
(c) aminocarbonyl,
(d) C$_{1-6}$alkoxy,
(e) C$_{1-6}$alkylcarbonyl,
(f) aryl or heteroaryl, as defined above;
(g) aryloxy or heteroaryloxy wherein the aryl or heteroaryl groups are defined above;
(h) aroyl or heteroaroyl wherein the aryl or heteroaryl groups are defined above;
(i)

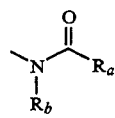

wherein R$_a$ and R$_b$ are each independently hydrogen; aryl or heteroaryl and mono and di-substituted aryl or heteroaryl as defined above; or substituted C$_{1-6}$ alkyl wherein the substitutent is selected from hydroxy, halo, and aryl or heteroaryl, or wherein R$_a$ and R$_b$ are joined together with the nitrogen and carbon atoms to which they are attached, to form a lactam or benzolactam ring wherein the lactam portion thereof is a ting of 5, 6, 7, or 8 atoms, said lactam or benzolactam containing a single hetero atom;
(j)

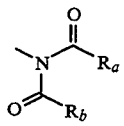

wherein R$_a$ and R$_b$ are each independently hydrogen; aryl or heteroaryl and mono and di-substituted aryl or heteroaryl as defined above; or substituted C$_{1-6}$ alkyl wherein the substitutent is selected from hydroxy, halo, and aryl, or wherein R$_a$ and R$_b$ are joined together with the nitrogen and carbon atoms to which they are attached to form a cyclic imide, or is benzofused onto a cyclic imide, wherein the cyclic imide portion thereof is a ring of 5, 6, 7, or 8 atoms, said cyclic imide containing a single hetero atom;
(k) amino or mono- or di-substituted amino wherein the substituents are independently selected from C$_{1-6}$ alkyl and aryl or heteroaryl as defined above;
(l)

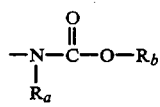

wherein R$_a$ and R$_b$ are each independently hydrogen; C$_{1-6}$ alkyl; aryl or heteroaryl as defined above; or wherein R$_a$ and R$_b$ are joined together with the nitrogen and oxygen atoms to which they are attached, to form a cyclic-carbamate, or a benzofused cyclic-carbamate, wherein the carbamate ring contains 5, 6, 7, or 8 atoms, said ring containing the two heteroatoms;
(m)

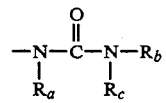

wherein R$_a$, R$_b$, and R$_c$ are each independently hydrogen; C$_{1-6}$ alkyl; aryl or heteroaryl as defined above; or wherein R$_a$ and R$_b$ are joined together with the nitrogen atoms to which they are attached to form a cyclic-urea or benzofused cyclic-urea, said urea ring containing 5, 6, 7, or 8 atoms and said two nitrogens;
(n)

wherein R$_a$ and R$_b$ are each independently hydrogen; C$_{1-6}$ alkyl; aryl or heteroaryl as defined above; or wherein R$_a$ and R$_b$ are joined together with the nitrogen and sulfur atoms to which they are attached, to form a cyclic-sulfonamide or benzofused cyclic-sulfonamide ring, said sulfonamide ting containing 5, 6, 7, or 8 atoms and said heteroatoms;
(o)

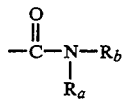

wherein R$_a$ and R$_b$ are each independently hydrogen; C$_{1-6}$ alkyl; aryl or heteroaryl as defined above; or wherein R$_a$ and R$_b$ are joined together with the nitrogen atom to which they are attached, to form a heterocycle or benzofused heterocycle ting, said ting containing 5, 6, 7, or 8 atoms and said nitrogen atom;
(p)

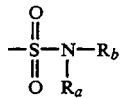

wherein R$_a$ and R$_b$ are each independently hydrogen; C$_{1-6}$ alkyl; aryl or heteroaryl as defined above; or wherein R$_a$ and R$_b$ are joined together with the nitrogen atom to which they are attached, to form a heterocycle or benzofused heterocycle ting, said ting containing 5, 6, 7, or 8 atoms and said nitrogen atom;
R$_3$ is
(a) mono- or di-substituted C$_{1-10}$alkylamino, or mono- or disubstituted di-C$_{1-10}$ alkyl amino wherein the substituents are selected from the group consisting of:
91) hydrogen,
(2) mercapto,
(3) hydroxy,
(4) carboxy,
(5) amino,
(6) aminocarbonyl,
(7) mono- or di-C$_{1-6}$alkyl amino,
(8) mono- or di-C$_{1-6}$alkyl aminocarbonyl,
(9) guanidino,
(10) aryl or heteroaryl, as defined above;
(b) an amino acid derivative of Formula II

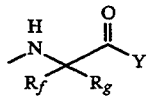

wherein $R_f$ and $R_g$ are individually selected from:
(a) hydrogen,
(b) $C_{1-6}$ alkyl,
(c) mercapto $C_{1-6}$ alkyl,
(d) hydroxy $C_{1-6}$ alkyl,
(e) carboxy $C_{1-6}$ alkyl,
(f) amino $C_{1-6}$ alkyl
(g) aminocarbonyl $C_{1-6}$ alkyl,
(h) mono- or di-$C_{1-6}$ alkyl amino $C_{1-6}$ alkyl,
(i) guanidino $C_{1-6}$ alkyl,
(j) substituted phenyl $C_{1-6}$ alkyl, wherein the substitutent is hydrogen, hydroxy, carboxy, $C_{1-4}$ alkyl, or $C_{1-4}$ alkyloxy,
(k) substituted indolyl $C_{1-6}$ alkyl, wherein the substitutent is hydrogen, hydroxy, carboxy, $C_{1-4}$ alkyl, or $C_{1-4}$ alkyloxy,
(l) substituted imidazolyl $C_{2-6}$ alkyl wherein the substimtent is hydrogen, hydroxy, carboxy, $C_{1-4}$ alkyl, or $C_{1-4}$ alkyloxy,
(m) substituted pyridyl $C_{1-6}$ alkyl wherein the substituent is hydrogen, hydroxy, carboxy, $C_{1-4}$ alkyl, or $C_{1-4}$ alkyloxy,
(n) substituted pyridylamino $C_{1-6}$ alkyl wherein the substitutent is hydrogen, hydroxy, carboxy, $C_{1-4}$ alkyl, or $C_{1-4}$ alkyloxy,
(o) substituted thiazolyl $C_{1-6}$ alkyl wherein the substimtent is hydrogen, hydroxy, carboxy, $C_{1-4}$ alkyl, or $C_{1-4}$ alkyloxy,
(p) substituted oxazolyl $C_{1-6}$ alkyl wherein the substimtent is hydrogen, hydroxy, carboxy, $C_{1-4}$ alkyl, or $C_{1-4}$ alkyloxy; and
Y is

wherein $R_6$ and $R_7$ are each individually selected from the group consisting of:
(a) H,
(b) $C_{1-10}$ alkyl,
(c) aryl, heteroaryl, aryl$C_{1-6}$ alkyl or heteroaryl$C_{1-6}$ alkyl, wherein the aryl or heteroaryl group is defined above.

DETAILED DESCRIPTION OF THE INVENTION

The invention encompasses compounds of Formula I and contains several preferred subclasses as described below.

A preferred class is a compound according to Formula I wherein Ar is an aryl or heteroaryl group selected from the group consisting of:
(1) phenyl,
(2) naphthyl,
(3) pyridyl,
(4) furyl,
(5) thienyl,
(6) isothiazolyl,
(7) isoxazolyl,
(8) thiazolyl,
(9) oxazolyl, which can be mono- or di-substituted with the substitutents independently selected from $C_{1-6}$ alkyl, halo, hydroxy, $C_{1-6}$ alkylcarbonyl, and aryl or heteroaryl are as defined above.

A preferred embodiment of this class is a compound according to Formula I furthermore wherein $R_1$ is OH, $OC_{1-6}$ alkyl, $OCH_2$phenyl.

Another class of preferred compounds is a compound according to Formula I wherein $R_2$ is hydrogen or mono- or disubstituted $C_{1-6}$alkyl or $C_{1-6}$ alkoxy, wherein the substituents are independently selected from the group consisting of:
(a) hydrogen,
(b) $C_{1-6}$alkoxy,
(c) aryl or heteroaryl, which is selected from the group consisting of
(1) phenyl,
(2) naphthyl,
(3) pyridyl,
(4) thienyl,
(5) imidazolyl,
(6) benzimidazolyl,
(7) benzofuryl,
(8) benzothienyl,
(9) indolyl,
(10) isoxazolyl,
(11) thiazolyl,
(12) oxazolyl,
(13) benzthiazolyl, and
(14) benzoxazolyl, which can be mono- or di-substituted with substitutents independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, and $C_{1-6}$alkylcarbonyl;
(d) aryloxy or heteroaryloxy wherein the aryl or heteroaryl groups are defined as in item (c) above;
(e) aroyl or heteroaroyl wherein the aryl or heteroaryl groups are defined as in item (c) above;
(f)

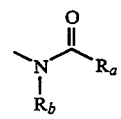

wherein $R_a$ and $R_b$ are each independently hydrogen; aryl or heteroaryl and mono and di-substituted aryl or heteroaryl as defined above in item (c); or substituted $C_{1-6}$alkyl wherein the substitutent is selected from hydroxy, halo, and aryl or heteroaryl, or wherein Ra and Rb are joined together with the nitrogen and carbon atoms to which they are attached, to form a lactam or benzolactam ring wherein the lactam portion thereof is a ring of 5, 6, 7, or 8 atoms, said lactam or benzolactam containing a single hetero atom;
(g)

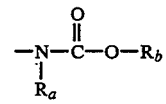

wherein $R_a$ and $R_b$ are each independently hydrogen; $C_{1-6}$ alkyl; aryl or heteroaryl as defined above in item (c);
(h)

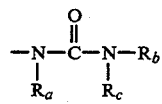

wherein $R_a$, $R_b$, and $R_c$ are each independently hydrogen; $C_{1-6}$ alkyl; aryl or heteroaryl as defined above in item (c);

(i)

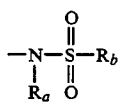

wherein $R_a$ and $R_b$ are each independently hydrogen; $C_{1-6}$ alkyl; aryl or heteroaryl as defined above in item (c);

(j)

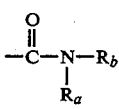

wherein $R_a$ and $R_b$ are each independently hydrogen; $C_{1-6}$ alkyl; aryl or heteroaryl as defined above in item (c); or wherein Ra and Rb are joined together with the nitrogen atom to which they are attached, to form a heterocycle or benzofused heterocycle ring, said ring containing 5, 6, 7, or 8 atoms and said nitrogen atom;

(k)

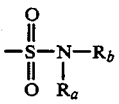

wherein Ra and Rb are each independently hydrogen; $C_{1-6}$ alkyl; aryl or heteroaryl as defined above in item (c); or wherein $R_a$ and $R_b$ are joined together with the nitrogen atom to which they are attached, to form a heterocycle or benzofused heterocycle ring, said ting containing 5, 6, 7, or 8 atoms and said nitrogen atom.

An another class is a compound according to Formula I wherein $R_3$ is substituted $C_{1-10}$alkylamino wherein the substituents are selected from the group consisting of:

(1) hydrogen,
(2) aminocarbonyl,
(3) mono- or di-$C_{1-6}$alkyl aminocarbonyl,
(4) aryl or heteroaryl, wherein the aryl or heteroaryl group is selected from the group consisting of:
  (a) phenyl,
  (b) naphthyl,
  (c) pyridyl,
  (d) thienyl,
  (e) imidazolyl,
  (f) benzimidazolyl,
  (g) benzofuryl,
  (h) benzothienyl,
  (i) indolyl,
  (j) isoxazolyl,
  (k) thiazolyl,
  (l) oxazolyl,
  (m) benzthiazolyl, and
  (n) benzoxazolyl,
which can be mono- or di-substituted with substituents independently selected from phenyl, $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, or $C_{1-6}$alkylcarbonyl.

A further preferred class is a compound according to Formula I wherein $R_3$ is an amino acid derivative of Formula II

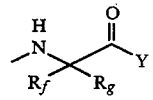

wherein $R_f$ is hydrogen and $R_g$ is selected from:
(a) $C_{1-6}$alkyl,
(b) amino $C_{1-6}$alkyl
(c) aminocarbonyl $C_{1-6}$alkyl,
(d) mono- or di-$C_{1-6}$alkyl amino $C_{1-6}$alkyl,
(e) guanidino $C_{1-6}$alkyl,
(f) substituted phenyl $C_{2-6}$alkyl, wherein the substimtent is hydrogen, hydroxy, carboxy, $C_{1-4}$alkyl, or $C_{1-4}$alkyloxy,
(g) substituted imidazolyl $C_{3-6}$alkyl wherein the substimtent is hydrogen, hydroxy, carboxy, $C_{1-4}$alkyl, or $C_{1-4}$alkyloxy,
(h) substituted pyridyl $C_{2-6}$alkyl wherein the substimtent is hydrogen, hydroxy, carboxy, $C_{1-4}$alkyl, or $C_{1-4}$alkyloxy,
(i) substituted pyridylamino $C_{3-6}$alkyl wherein the substitutent is hydrogen, hydroxy, carboxy, $C_{1-4}$alkyl, or $C_{1-4}$ alkyloxy,
(j) substituted thiazolyl $C_{2-6}$alkyl wherein the substitutent is hydrogen, hydroxy, carboxy, $C_{1-4}$alkyl, or $C_{1-4}$alkyloxy,
(k) substituted oxazolyl $C_{2-6}$alkyl wherein the substitutent is hydrogen, hydroxy, carboxy, $C_{1-4}$ alkyl, or $C_{1-4}$alkyloxy.

A subclass of this class is a compound according to Formula I wherein Formula It is an amino acid selected from alanine, valine, leucine, isoleucine, α-tert-butyl glycine, norleucine, serine, threonine, asparagine, glutamine, lysine, homohistidine, arginine, homophenylalanine, homotyrosine, methionine, omithine, homoserine, and citrulline.

A still further subclass is a compound according to Formula I, wherein Formula II,
Y is

wherein $R_6$ is hydrogen and $R_7$ is selected from the group consisting of:
(a) $C_{1-10}$alkyl,
(b) aryl, heteroaryl, aryl$C_{1-6}$alkyl or heteroaryl$C_{1-6}$alkyl, wherein the aryl or heteroaryl group is selected from the group consisting of
  (1) phenyl,
  (2) naphthyl,
  (3) pyridyl,
  (4) thienyl,
  (5) imidazolyl,
  (6) benzimidazolyl,
  (7) benzofuryl,
  (8) benzothienyl,
  (9) indolyl,
  (10) isoxazolyl,
  (11) thiazolyl,
  (12) oxazolyl,

(13) benzthiazolyl, and
(14) benzoxazolyl,
and mono- and di-substituted aryl and heteroaryl groups as defined above in items (1) to (14) wherein the substitutents are independently selected from phenyl, $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, or $C_{1-6}$alkylcarbonyl.

A preferred embodiment of this class is a compound according to Formula I wherein Ar is 4-propylphenyl or 4-biphenyl.

A still further subclass is a compound according to the Formula:

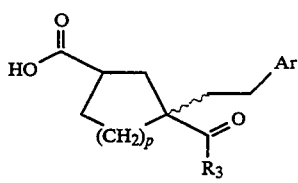

Ia wherein:
p is 1—2;
Ar is 4-propylphenyl or 4-biphenyl;
$R_3$ is an amino derivative of Formula It wherein said amino acid is selected from alanine, valine, leucine, isoleucine, norleucine, α-tert-butyl glycine, serine, threonine, asparagine, glutamine, lysine, homohistidine, arginine, homophenylalanine, homotyrosine, methionine, ornithine, homose fine, or citrulline; wherein said Y in Formula II is NH-Phenyl.

Specific embodiments according to Formula I are the compounds:

(a) 1-(2-(4-Propylphenyl)ethyl)cyclopentane-1,3-dicarboxylic acid 1-(L-leucine N-phenylamide) amide;
(b) 1-(2-(4-Propylphenyl)ethyl)cyclohexane-1,3-dicarboxylic acid 1-(L-leucine N-phenylamide) amide.

This invention also concerns a pharmaceutical composition and a method of treatment of stromelysin-mediated or implicated disorders or diseases (as described above) in a patient (which shall be defined to include man and/or mammalian animals raised in the dairy, meat, or fur industries or as pets) in need of such treatment comprising administration of the stromelysin inhibitors of Formula I as the active constituents.

Similarly, this invention also concerns pharmaceutical compositions and methods of treatment of collagenase mediated or implicated disorders or diseases (as described above) in a patient in need of such treatment comprising administration of the collagenase inhibitors of Formula I as the active constituents.

Similarly, this invention also concerns pharmaceutical compositions and methods of treatment of gelatinase-mediated or implicated disorders or diseases (as described above) in a patient in need of such treatment comprising administration of the gelatinase inhibitors of Formula I as the active constituents.

Moreover the invention also encompasses compositions, treatment, and method for co-administration of a compound of Formula I with a PMN elastase inhibitor such as those described in EP 0 337 549 which published on Oct. 18, 1989, which is hereby incorporated by reference.

Compounds of the instant invention are conveniently prepared using the procedures described generally below in Scheme I and more explicitly described in the Example section thereafter.

SCHEME I

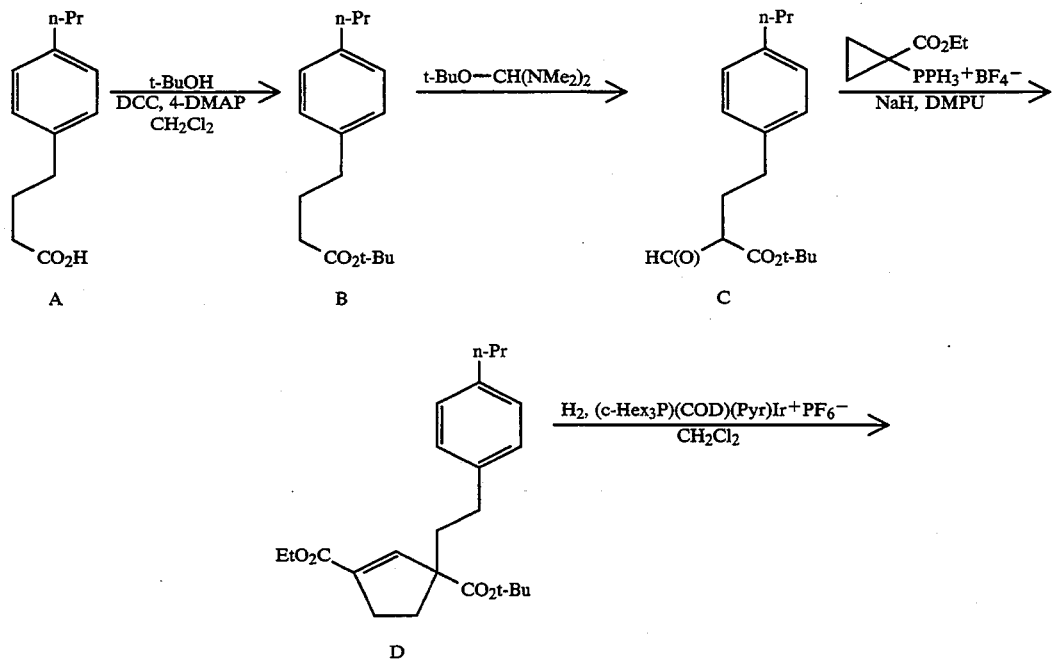

-continued
SCHEME I

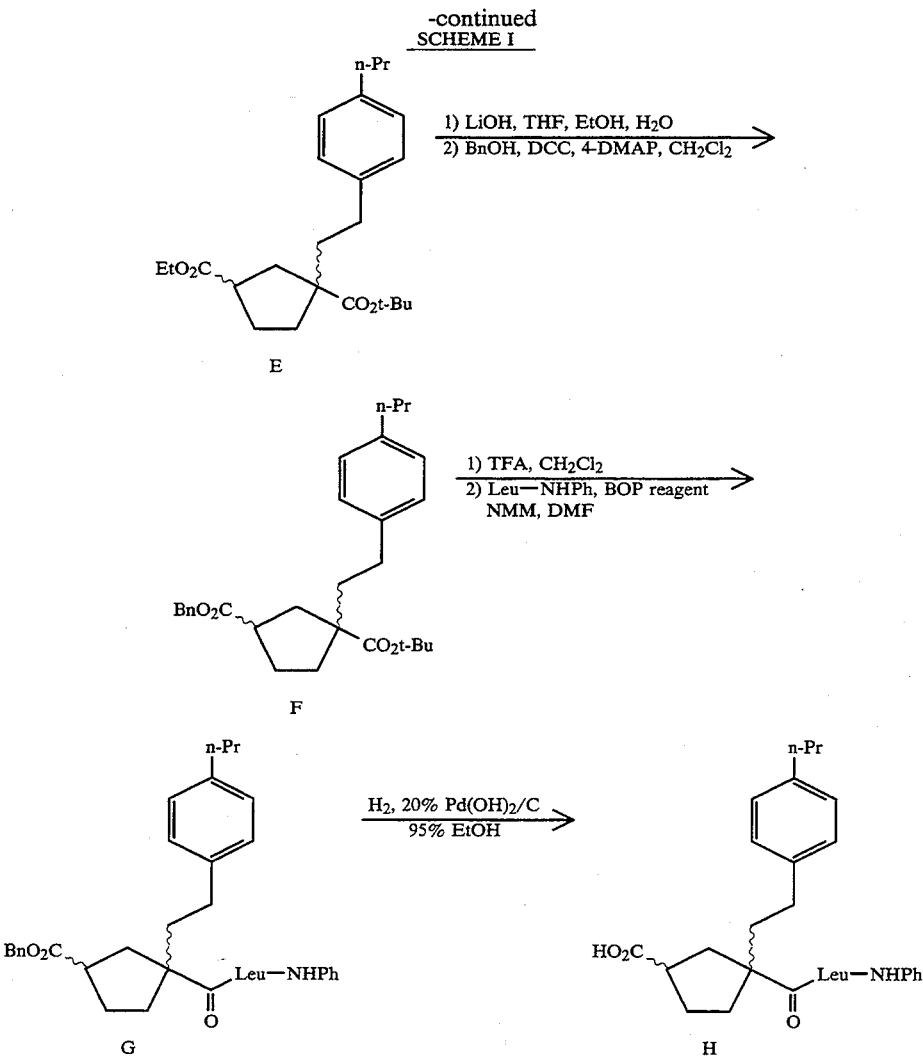

The tert-butyl ester B of 4-(4-propylphenyl)butanoic acid A is prepared by reaction with tert-butyl alcohol in the presence of a condensing agent, eg. dicyclohexylcarbodiimide (DCC), and 4-dimethylaminopyridine (4-DMAP). This ester B is formylated with tert-butoxybis(dimethylamino)methane to form t-butyl 2-formyl-4-(4-propylphenyl)butanoate C. According to the method described in the literature (P. L. Fuchs et al., *J. Org. Chem.* 1974, 96, 1607–9), the enolate of C is formed with sodium hydride and is reacted with 1-carboethoxycyclopropyl triphenylphosphonium tetrafluoroborate to form cyclopentene derivative D. Selective reduction of C is affected by hydrogenation in the presence of (tricyclohexylphosphine)( 1,5-cyclooctadiene)(pyridine )iridium(I) hexafluorophosphate catalyst to afford the substituted cyclopentane E. The ethyl ester in E is convened to the benzyl ester F by basic hydrolysis followed by esterification with benzyl alcohol. The t-butyl ester in F is deprotected by treatment with strong acid (eg. trifluoroacetic acid or hydrochloric acid) followed by condensation with an amino acid derivative, in this case, L-leucine N-phenylamide, to form G. Catalytic hydrogenolysis of the benzyl ester affords the cyclopentane carboxylic acid H. Anyone skilled in the art would recognize that this scheme is representative of methodology that could be applied to the preparation of a variety of cyclopentane carboxylic acids of the type H by replacing A with other aryl alkanoic acids and replacing L-leucine N-phenylamide with other amino acid derivatives.

SCHEME II

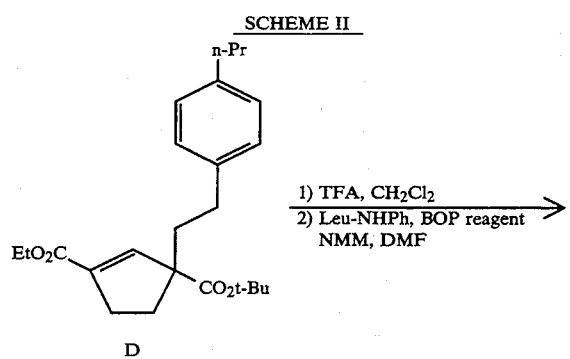

-continued
SCHEME II

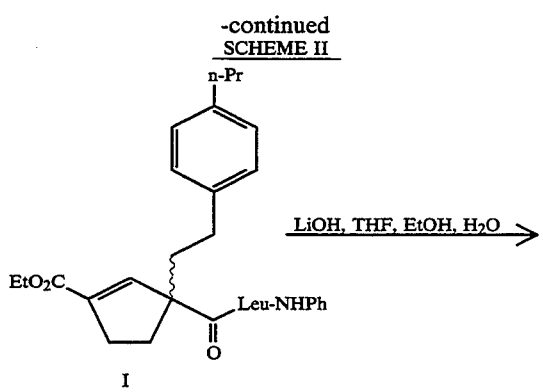

The t-butyl ester of cyclopentene D (prepared by methodology outline in Scheme I) is hydrolyzed in the presence of strong acid (eg. trifluoroacetic acid or hydrochloric acid) followed by reaction with an amino acid derivative, in this case L-leucine N-phenylamide, to form I. Basic aqueous hydrolysis of I yields cyclopentene-carboxylic acid J. Catalytic hydrogenolysis of the double bond in J would yield the cyclopentane acid H. Anyone skilled in the art would recognize that this scheme is representative of methodology that could be applied to the preparation of a variety of cyclopentene carboxylic acids of the type J by replacing A from Scheme I with other aryl alkanoic acids and replacing L-leucine N-phenylamide with other amino acid derivatives.

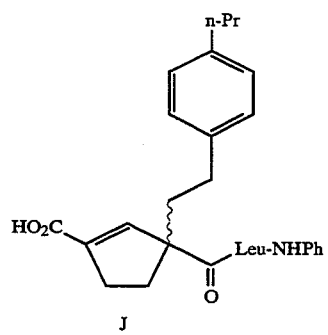

SCHEME III

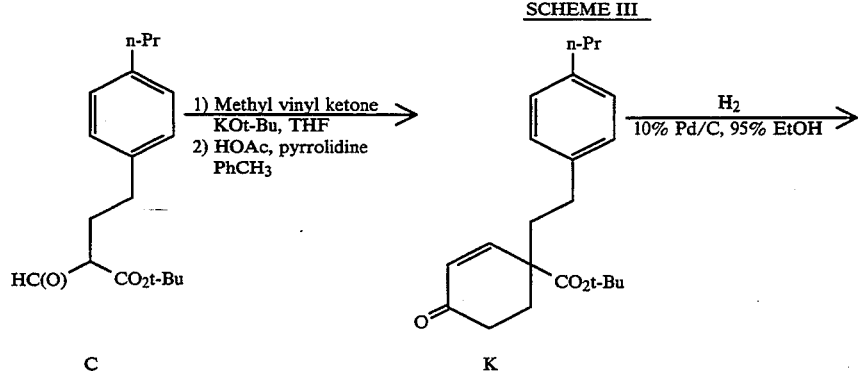

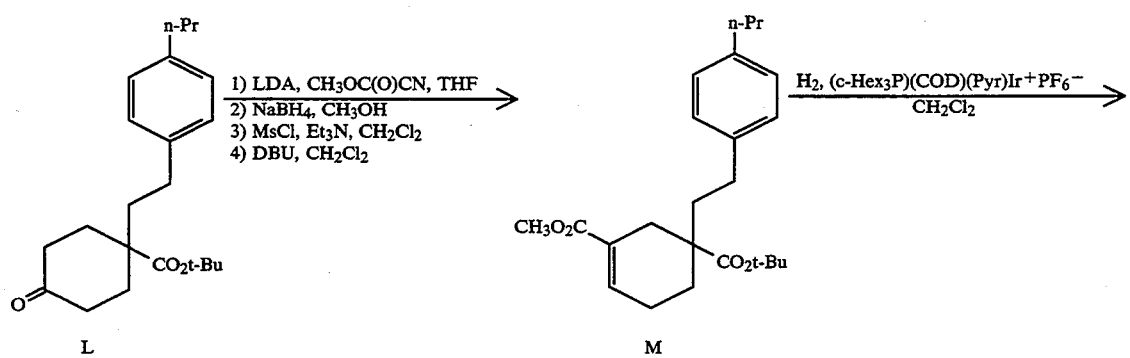

-continued
SCHEME III

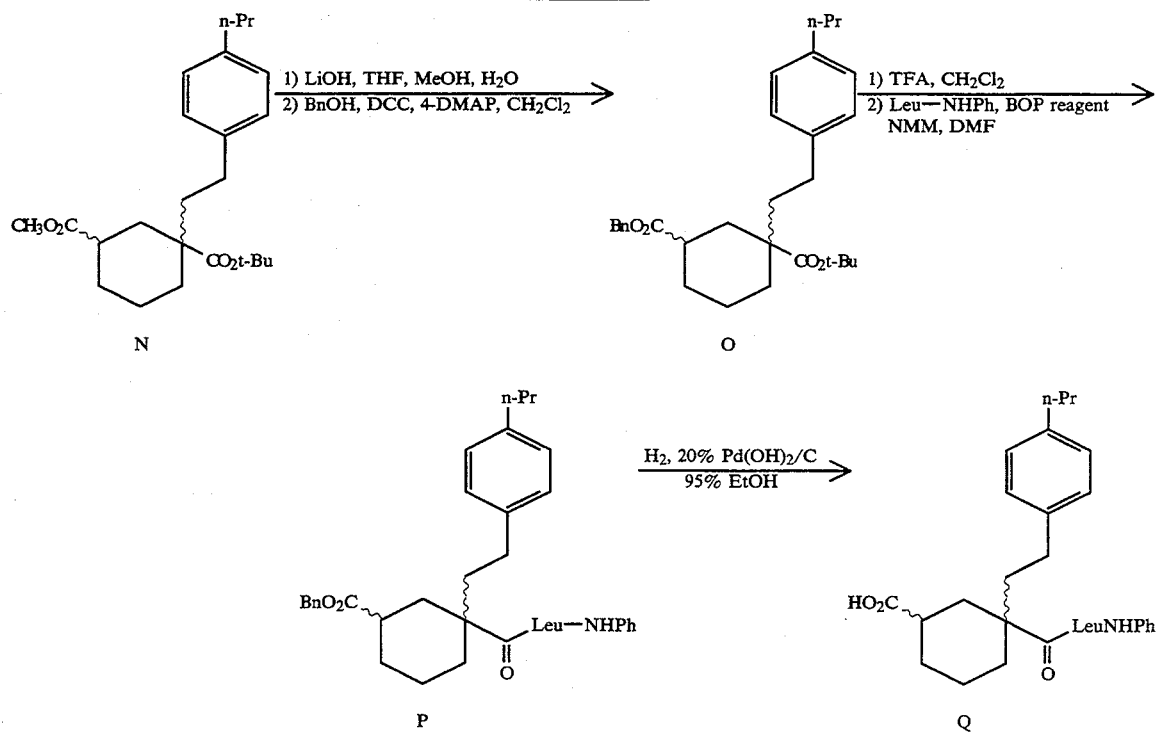

The formyl ester C is reacted with methyl vinyl ketone in the presence of base followed by cyclization and elimination to form cyclohexenone K. Catalytic hydrogenation affords cyclohexanone L which is acylated in the presence of strong base with methyl cyanoformate to form a ketoester. Reduction of the ketone, followed by sulfonylation of the resultant alcohol with mesyl chloride, and then base catalyzed elimination yields cyclohexene 1,3-diester M. Catalytic hydrogenation of the double bond in the presence of (tricyclohexyl-phosphine)(1,5-cyclooctadiene)(pyridine)iridium(I) hexafluoro-phosphate catalyst affords cyclohexane 1,3-diester N. Methyl ester hydrolysis followed by condensation with benzyl alcohol yields diester O. t-Butyl ester hydrolysis followed by condensation with an amirto acid derivative in the presence of benzotriazol-1-yloxy-tris(dimethylamino)phosphonium hexafluorophosphate (BOP) affords cyclohexane P. Catalytic hydrogenolysis of the benzyl ester in P affords cyclohexane-carboxylic acid Q. Anyone skilled in the art would recognize that this scheme is representative of methodology that could be applied to the preparation of a variety of cyclohexane-carboxylic acids of the type Q by replacing A from Scheme I with other aryl alkanoic acids and replacing L-leucine N-phenylamide with other amino acid derivatives.

SCHEME IV

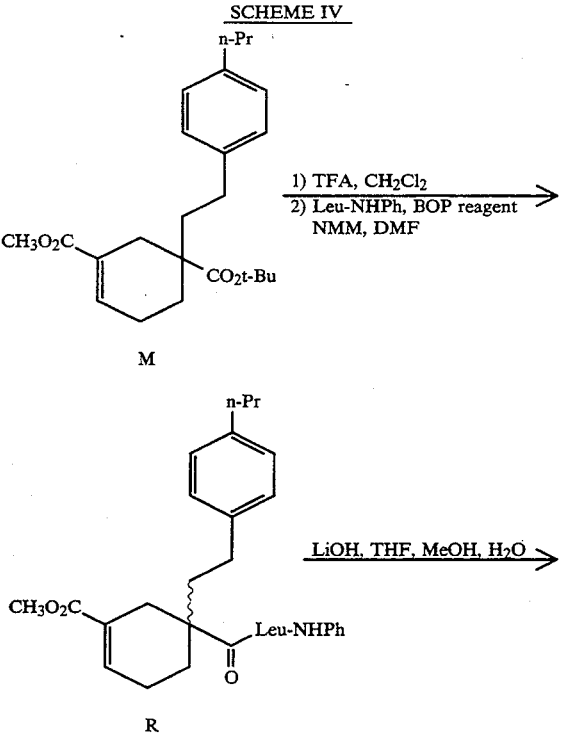

-continued
SCHEME IV

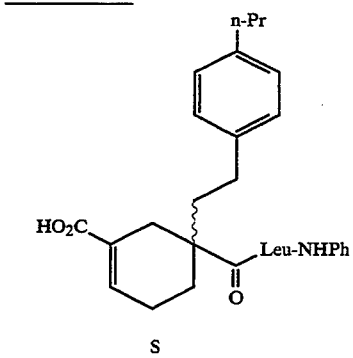

The t-butyl ester of cyclohexene M (prepared by methodology outlined in Scheme III) is hydrolyzed in the presence of strong acid (eg. trifluoroacetic acid or hydrochloric acid) followed by reaction with an amino acid derivative, in this case L-leucine N-phenylamide, to form R. Basic aqueous hydrolysis of R yields cyclohexene-carboxylic acid S. Catalytic hydrogenolysis of the double bond in S yields the cyclohexane acid Q. Anyone skilled in the art would recognize that this scheme is representative of methodology that could be applied to the preparation of a variety of cyclohexene-carboxylic acids of the type S by replacing A from Scheme I with other aryl alkanoic acids and replacing L-leucine N-phenylamide with other amino acid derivatives.

The following examples are intended to illustrate the preparation of compounds of Formula I, and as such are not intended to limit the invention as set forth in the claims appended, thereto.

EXAMPLE 1

1-(2-(4-Propylphenyl)ethyl)cyclopentane-1,3-dicarboxylic acid 1-(L-leucine phenylamide) amide Step A:

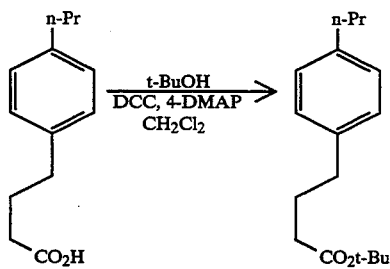

tert-Butyl 4-(4-propylphenyl)butanoate. [The preparation of 4-(4-propylphenyl)butanoic acid, is described in the chemical literature: see L. I. Smith and C. -P. Lo, *J. Am. Chem. Soc.*, 1948, 70, 2209–15 (Chem. Abstr. 42:7753c)].

4-(Dimethylamino)pyridine.(265 mg, 2.17 mmol) was added to a solution of 4-(4-propylphenyl)butanoic acid (3.00 g, 14.5 mmol) and tert-butanol (4.10 mL, 3.22 g, 43.5 mmol) in dichloromethane (20 mL). The reaction was cooled to 0° C. and a solution of 1,3-dicyclohexylcarbodiimide (3.59 g, 17.3 mmol) in dichloromethane (5.0 mL) was added over 10 min. The reaction was allowed to slowly warm to room temperature and was stirred for 24 h. Additional 1,3-dicyclohexylcarbodiimide (1.20 g, 5.82 mmol) was added and the reaction was stirred at room temperature of for 40 h. Water (3 mL) was added and the mixture was stirred for 15 min before being filtered. The precipitate was washed with hexane (25 mL) and the combined tiltrate was washed with 2 N aq. HCl (25 mL), saturated aq. $NaHCO_3$ (25 mL), and saturated aq. NaCl (2×25 mL). The organic layer was dried ($Na_2SO_4$), filtered, and evaporated. Purification by flash column chromatography on silica gel (110 g) eluting with 1 L of 5% $Et_2O$/hexane gave 2.90 g (76% yield) of the title compound as a colorless oil. NMR (400 MHz, $CDCl_3$): δ7.10 (s, 4H), 2.60 (t, 2H, J=7 Hz), 2.55 (t, 2H, J=7 Hz), 2.23 (t, 2H, J=7 Hz), 1.89 (quintet, 2H, J=7 Hz), 1.62 (sextet, 2H, J=7 Hz), 1.45 (s, 9H), 0.94 (t, 3H, J=7 Hz).

Step B:

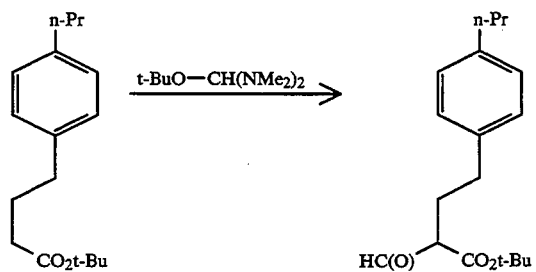

tert-Butyl 2-formyl-4-(4-propylphenyl)butanoate. A solution of 1.00 g (3.81 mmol) of tert-butyl 4-(4-propylphenyl)butanoate in tert-butoxybis(dimethylamino)methane (10.0 mL, 8.44 g, 48.4 mmol) was warmed in an oil bath at 120° C. for 71 h. The solution was allowed to cool to room temperature before being poured into a 0° C. solution containing water (12.5 mL) and concentrated aq. HCl (8.25 mL) dissolved in methanol (150 mL). After 5 min., the mixture was concentrated on a rotary evaporator and the residue was partitioned between EtOAc (75 mL) and 2 N aq HCl (40 mL). The organic layer was washed with saturated aq. NaCl (2×35 mL), dried ($Na_2SO_4$), decanted, and evaporated. The residue was purified by flash column chromatography on silica gel (57 g), eluting with 500 mL of 5% $Et_2O$/hexane followed by 250 mL of 10% $Et_2O$/hexane. The starting ester (0.57 g, 57% recovery) was eluted before the title compound, isolated as a colorless oil (0.36 g, 32% yield).

NMR (400 MHz, $CDCl_3$) indicated the presence of the product as a 2:1 mixture of the enol and aldehyde tautomers, respectively. Enol tautomer: δ11.57 (d, 1H, J=12 Hz), 7.09 d, 2H, J=8 Hz), 7.05 (d, 2H, J=8 Hz), 6.90 (d, 1H, J=12 Hz), 2.66 (t, 2H, J=7 Hz), 2.55 (t, 2H, J=7 Hz), 2.27 (t, 2H, J=7 Hz), 1.62 (sextet, 2H, J=7 Hz), 1.54 (s, 9H); 0.94 (t, 3H, J=7 Hz). Aldehyde tautomer (partial data): d 9.68 (d, 1H, J=2 Hz), 7.12–7.07 (m, 4H), 3.20 (td, 1H, J=7, 2 Hz), 2.13 (q, 1H, J=7 Hz), 1.50 (s, 9H).

Step C:

(q, 2H, I=7 Hz), 2.71–2.43 (m, 4H), 2.55 (t, 2H, J=7 Hz), 2.06–1.88 (m, 4H), 1.62 (sextet, 2H, J=7 Hz), 1.48 (s, 9 H), 1.31 (t, 3H, J=7 Hz), 0.93 (t, 3H, J=7 Hz).

Step D:

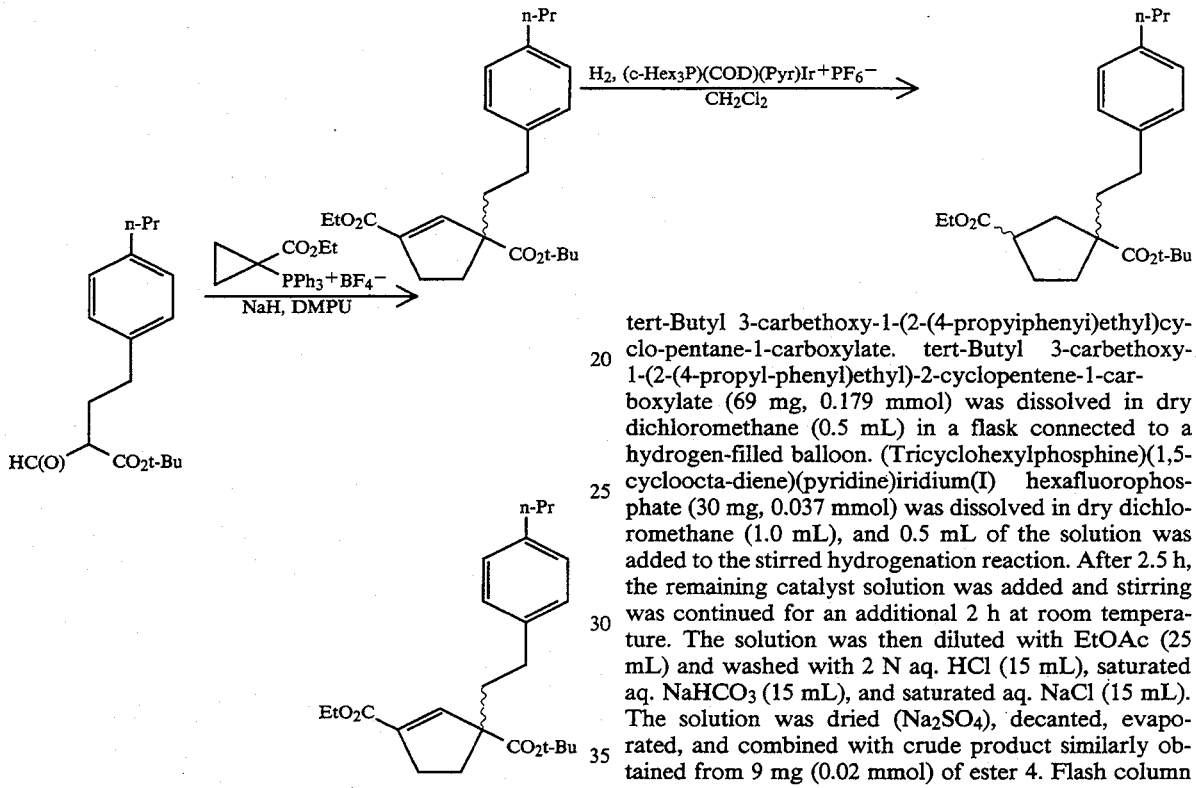

tert-Butyl 3-carbethoxy-1-(2-(4-propylphenyl)ethyl)-2-cyclopentene-1-carboxylate. Sodium hydride (16 mg of 60% oil dispersion, 0.40 mmol) was added to a solution of 102 mg (0.35 mmol) of tert-butyl 2-formyl-4-(4-propylphenyl)butanoate in 1,3-dimethyl-3,4,5,6-tetrahydro-2(1H)-pyrimidinone (1.5 mL). After 20 min., 1-carboethoxycyclopropyl triphenylphosphonium tetrafluoroborate (193 mg, 0.42 mmol) was added to the pale yellow solution and stirring was continued overnight at room temperature. The solution was then partitioned between hexane (25 mL) and 2N aq. HCl (25 mL). The organic layer was washed with water (15 mL) and saturated aq. NaCl (15 mL), dried (Na2SO4), decanted, and evaporated. The residue was purified by flash column chromatography on silica gel (8 g), eluting with 100 mL of 5% EtOAc/hexane, to give the title compound as 52 mg (38% yield) of colorless oil.

NMR (400 MHz, CDCl3): δ7.10 (d, 2H, J=8 Hz), 7.04 (d, 3H, J=8 Hz), 6.72 (t, 1H, J=1.5 Hz), 4.21 tert-Butyl 3-carbethoxy-1-(2-(4-propyiphenyi)ethyl)cyclo-pentane-1-carboxylate. tert-Butyl 3-carbethoxy-1-(2-(4-propyl-phenyl)ethyl)-2-cyclopentene-1-carboxylate (69 mg, 0.179 mmol) was dissolved in dry dichloromethane (0.5 mL) in a flask connected to a hydrogen-filled balloon. (Tricyclohexylphosphine)(1,5-cycloocta-diene)(pyridine)iridium(I) hexafluorophosphate (30 mg, 0.037 mmol) was dissolved in dry dichloromethane (1.0 mL), and 0.5 mL of the solution was added to the stirred hydrogenation reaction. After 2.5 h, the remaining catalyst solution was added and stirring was continued for an additional 2 h at room temperature. The solution was then diluted with EtOAc (25 mL) and washed with 2 N aq. HCl (15 mL), saturated aq. NaHCO3 (15 mL), and saturated aq. NaCl (15 mL). The solution was dried (Na2SO4), decanted, evaporated, and combined with crude product similarly obtained from 9 mg (0.02 mmol) of ester 4. Flash column chromatography twice on silica gel (10 g) eluting with 200 mL of 3% EtOAc/hexane gave 47 mg (60% yield) of the more mobile stereoisomer of the title compound along with 24 mg (31% yield) of the less mobile stereoisomer.

NMR (400 MHz, CDCl3) of the more mobile product: δ7.09 (d, 2H, J=8 Hz), 7.06 (d, 2H, J=8 Hz), 4.13 (q, 2H, J=7 Hz), 2.89 (quintet, 1H, J=7 Hz), 2.58–2.43 (m, 5 H), 2.16 (dt, 1H, J=12, 6 Hz), 2.05–1.83 (m, 4H), 1.71 (dd, 1H, J=13, 9 Hz), 1.67–1.57 (m, 3H), 1.48 (s, 9H), 1.25 (t, 3H, J=7 Hz), 0.93 (t, 3H, J=7 Hz).

Step E:

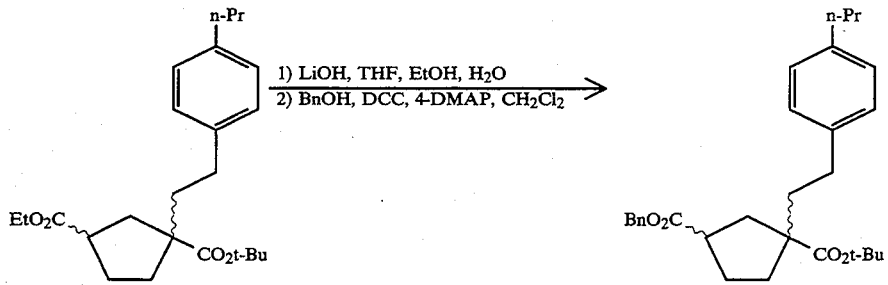

tert-Butyl 3-carbobenzyloxy-1-(2-(4-propylphenyl)ethyl)-cyclopentane-1-carboxylate. tert-Butyl 3-carbethoxy-1-(2-(4-propylphenyl)ethyl)cyclopentane-1-carboxylate (41 mg, 0.11 mmol) was dissolved in a mixture of THF (2.1 mL) and 95% ethanol (1.4 mL), and 0.5 N aq. LiOH (0.70 mL, 0.35 mmol) was added. After being stirred for 3 h at room temperature, the contents of the reaction flask was partitioned between EtOAc (40 mL) and 2 N aq. HCl (20 mL). The organic layer was washed with saturated aqueous NaCl (20 mL), dried (Na2SO4), decanted, and evaporated to give 39 mg of colorless film. This was combined with 5 mg of crude carboxylic acid obtained similarly from 6 mg of tert-butyl 3-carbethoxy-1-(2-(4-propylphenyl)-ethyl)cyclopentane-1-carboxylate and used directly in the esterification reaction.

Benzyl alcohol (0.025 mL, 26 mg, 0.24 mmol) and 4-(dimethylamino)pyridine (3 mg, 0.02 mmol) were added to a solution of the crude carboxylic acid (44 mg, 0.12 mmol) in dichloromethane (0.50 mL). A solution of 1,3-dicyclohexylcarbodiimide (32 mg, 0.16 mmol) in dichloromethane (0.10 mL) was added and the mixture was stirred 4 h at room temperature. Water (3 drops) and hexane (1.5 mL) were added and the mixture was filtered after 10 min. The precipitate was rinsed with hexane (5 mL) and the combined filtrate was diluted with hexane (15 mL) and washed with 2 N aq. HCl (10 mL) and saturated aq. NaCl (10 mL). The solution was dried (Na2SO4), decanted, and evaporated. The crude product was purified by flash column chromatography on silica gel (2.5 g) eluting with 100 mL of 5% EtOAc/hexane to give 52 mg (95% yield) of the title compound as a colorless oil. NMR (400 MHz, CDCl3): δ7.39–7.29 (m, 5H), 7.09 (d, 2H, J=8 Hz), 7.06 (d, 2H, J=8 Hz), 5.12 (s, 2H), 2.96 (quintet, 1H, J=8 Hz), 2.57–2.42 (m, 5 Hz), 2.16 (dt, 1H, J=12, 6 Hz), 2.05–1.82 (m, 4H), 1.74 (dd, 1H, J=13, 9 Hz), 1.67–1.57 (m, 3H), 1.47 (s, 9H), 0.94 (t, 3H, J=7 Hz).

Step F:

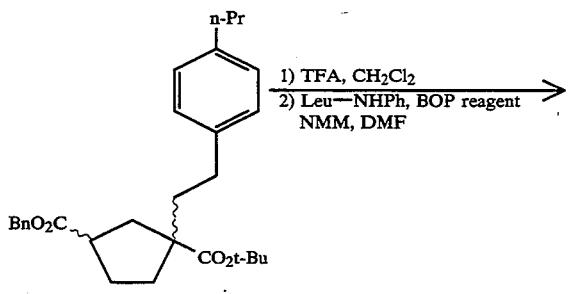

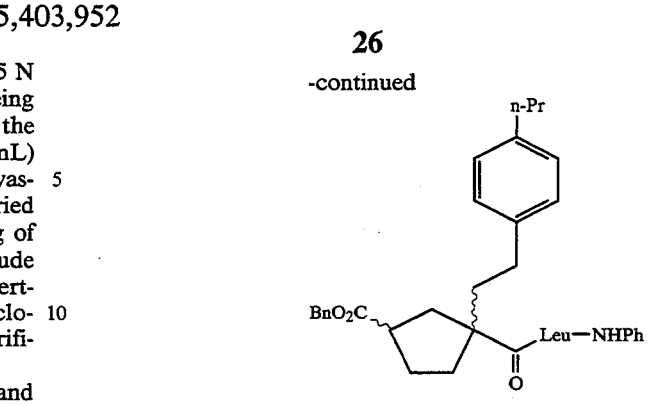

3-Carbobenzyloxy-1-(2-(4-propylphenyl)ethyl)cyclopentane-1-carboxylic acid (L-leucine phenylamide) amide.

Trifluoroacetic acid (2.0 mL, 3.0 g, 26 mmol) was added to a stirred 0° C. solution of 52 mg (0.12 mmol) of tert-butyl 3-carbobenzyloxy-1-(2-(4-propylphenyl)ethyl)cyclopentane-1-carboxylate in dichloromethane (2.0 mL). After 2.5 h, toluene (2.0 mL) was added and the solution was evaporated to give crude carboxylic acid as 45 mg of pale yellow oil.

The crude carboxylic acid (45 mg, 0.11 mmol) was dried by evaporation of a toluene solution and then dissolved in DMF (0.40 mL). Molecular sieves (4 Å, 0.16 g) and N-methylmorpholine (0.027 mL, 25 mg, 0.25 mmol) were added. After 10 min., benzotfiazol-1-yloxy-tris(dimethylamino)phosphonium hexafluorophosphate (60 mg, 0.14 mmol) was added and the solution was stirred for 40 min. before the addition of L-leucine anilide (28 mg, 0.14 mmol). After 1.5 h at room temperature, the solution was diluted with 20 mL of EtOAc and washed with 2 N aq. HCl (10 mL), saturated aq. NaHCO3 (10 mL), and saturated aq. NaCl (10 mL). The organic layer was dried (Na2SO4), decanted, and evaporated. Purification by flash column chromatography on silica gel (4.7 g) eluting with 100 mL of 3% EtOAc/dichloromethane gave 55 mg (83% yield) of the title compound as a colorless film. NMR (400 MHz, CDCl3) indicated a 1:1 mixture of diastereomers: δ8.50 (s, 1 H), 7.47 (d, 2H, J=7 Hz), 7.38–7.29 (m, 5H), 7.25 (t, 2H, J=7 Hz), 7.06 (t, 1H, J=7 Hz), 7.04 (d, 1H, J=8 Hz), 7.02 (d, 1H, J=8 Hz), 6.96 (d, 1H, J=8 Hz), 6.93 (d, 1H, J=8 Hz), 6.21 (d, 0.5H, J=8 Hz), 6.16 (d, 0.5H, J=8 Hz), 5.11 (s, 2H), 4.66 (bq, 1H, J=7 Hz), 2.95 (quintet, 0.5 H, J=8 Hz), 2.92 (quintet, 0.5H, J=8 Hz), 2.60–2.37 (m, 5H), 2.16–2.06 (m, 1H), 2.00–1.54 (m, 11H), 0.99 (d, 3H, J=6 Hz), 0.97 (d, 1.5H, J=6 Hz), 0.96 (d, 1.5 H, J=6 Hz), 0.93 (t, 1.5H, J=7 Hz), 0.92 (t, 1.5H, J=7 Hz).

Step G:

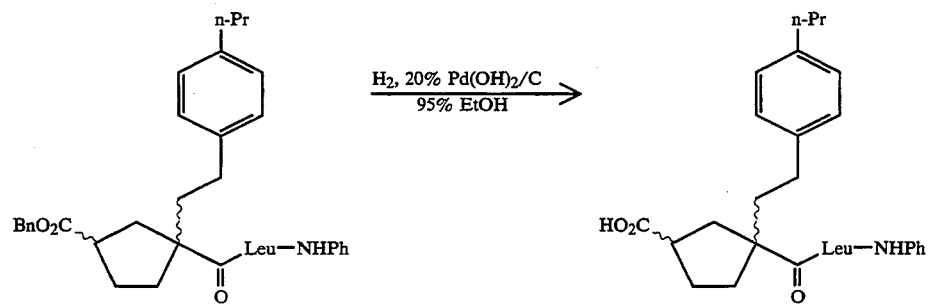

1-( 2-( 4-Propylphenyl)ethyl)cyclopentane-1,3-dicarboxylic acid 1-(L-leucine phenylamide) amide. Catalyst (7 mg of 20% Pd(OH)$_2$/C.) was added to a solution of 3-carbobenzyloxy-1-(2-(4-propylphenyl)ethyl)cyclopentane-1-carboxylic acid (leucine phenylamide) amide (55 mg, 0.94 mmol) in 95% ethanol (2.0 mL) and the mixture was stirred at room temperatam for 2.5 h in a flask connected to a hydrogen-filled balloon. The mixture was centrifuged and the supematant was filtered through a 0.45 micron membrane. The catalyst was rinsed with additional 95% ethanol and the combined flitrate was evaporated to give 46 mg ( 100% yield) of the title compound as a colorless brittle glass.

NMR (400 MHz, CDCl$_3$) indicated a 1:1 mixture of diastereomers: δ8.82 (s, 0.5 H), 8.66 (s, 0.5H), 7.49 (d, 2H, J=7 Hz), 7.25 (t, 2H, J=7 Hz), 7.06 (bt, 1H, J=7 Hz), 7.02 (d, 2H, J=8 Hz), 6.95 (d, 1H, J=8 Hz), 6.94 (d, 1H, J=8 Hz), 6.76 (d, 0.5 H, J=8 Hz), 6.70 (d, 0.5H, J=8 Hz), 4.74 (bq, 1H, J=7 Hz), 2.95–2.84 (m, 1H), 2.58 (dd, 0.5H, J=13, 8 Hz), 2.54–2.36 (m, 2.5H), 2.50 (t, 2H, J=7 Hz), 2.19–2.06 (m, 1H), 2.01–1.66 (m, 9H), 1.58 (sextet, 2H, J=7 Hz), 0.98 (d, 3H, H=6 Hz), 0.96 (d, 1.5 H, J=6 Hz), 0.95 (1.5 H, J=6 Hz), 0.91 (t, 3H, J=7 Hz).

EXAMPLE 2

1-(2-(4-Propylphenyl)ethyl)-2-cyclopentene-1,3-dicarboxylic acid 1-(leucine phenylamide) amide Step A:

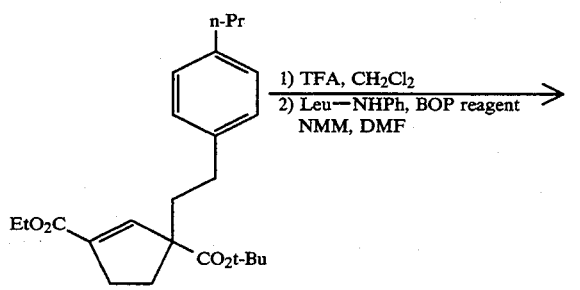

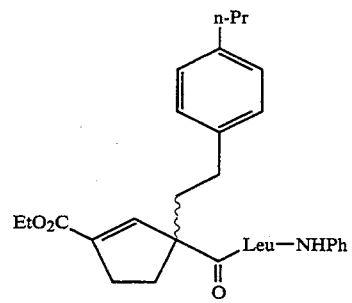

3-Carbethoxy-1-(2-(4-propylphenyl)ethyl)-2-cyclopentene-1-carboxylic acid (leucine phenylamide) amide. Trifluoroacetic acid (4.0 mL, 6.0 g, 52 mmol) was added to a stirred 0° C. solution of 53 mg (0.14 mmol) of tert-butyl 3-carbethoxy-1-(2(4-propylphenyl)-ethyl)-2-cyclopentene- 1-carboxylate in dichloromethane (4.0 mL). After 2 h, toluene (5.0 mL) was added and the solution was evaporated to give crude carboxylic acid as 45 mg of colorless oil.

The crude carboxylic acid was dried by evaporation of a toluene solution and then dissolved in dimethylformamide (0.50 mL). Molecular sieves (4 Å, 0.23 g) and N-methylmorpholine (0.035 mL, 32 mg, 0.32 mmol) were added. After 10 min., benzotriazol-1-yloxytris-(dimethylamino)phosphonium hexafluorophosphate (80 mg, 0.18 mmol) was added and the solution was stirred for 40 min. before the addition of L-leucine anilide (37 mg, 0.18 mmol). After 2 h at room temperature, the solution was diluted with 30 mL of ethyl acetate and washed with 2 N aq. hydrochloric acid (20 mL), saturated aq. sodium bisulfate (20 mL), and saturated aq. sodium chloride (20 mL). The organic layer was dried over anhydrous sodium sulfate, decanted, and evaporated. Purification by flash column chromatography on silica gel (5 g) eluting with 150 mL of 1.5% ethyl acetate/dichloromethane followed by 50 mL of 3% ethyl acetate/dichloromethane gave 53 mg (73% yield) of the title compotmd as a colorless oil.

$^1$H-NMR (400 MHz, CDCl$_3$) indicated a 1:1 mixture of diastereomers: δ8.51 (s, 0.5H), 8.47 (s, 0.5H), 7.50 (d, 1H, J=7 Hz), 7.48 (d, 1H, J=7 Hz), 7.27 (t, 2H, J=7 Hz), 7.11–7.00 (m, 4H), 6.98 (d, 1H, J=7 Hz), 6.78 (t, 0.5H, J=1.5 Hz), 6.76 (t, 0.5H, J=1.5 Hz), 6.06 (d, 0.6H, J=7 Hz), 6.04 (d, 0.5H, J=7 Hz), 4.68–4.60 (m, 1H), 4.23 (q, 2H, J=6 Hz), 2.68–2.58 (m, 2H), 2.56–2.42 (m, 4H), 2.40–2.25 (m, 1H), 2.23–2.12 (m, 1H), 2.09–1.99 (m, 1H), 1.96–1.56 (m, 6H), 1.32 (t, 3H, J=6 Hz), 0.99 (d, 1.5H, J=6 Hz), 0.97 (d, 1.5H, J=6 Hz), 0.96 (d, 1.5H, J=6 Hz), 0.95 (d, 1.5H, J=6 Hz), 0.93 (t, 1.5 H, J=7 Hz), 0.92 (t, 1.5H, J=7 Hz).

Step B:

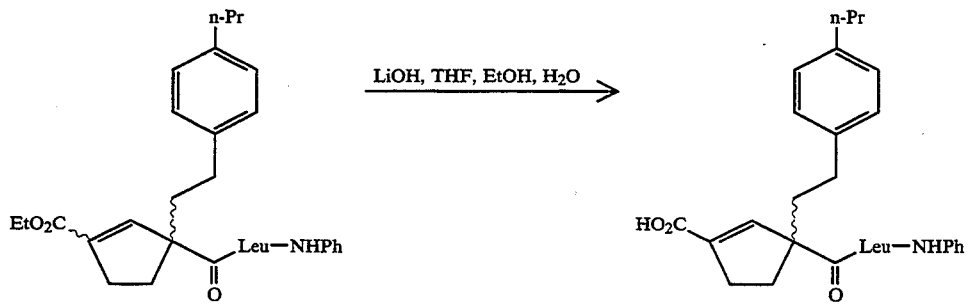

1-(2-(4-Propylphenyl)ethyl)-2-cyclopentene-1,3-dicarboxylic acid 1-(leucine phenylamide) amide. 3-Carbethoxy-1-(2-(4-propylphenyl)ethyt)-2-cyclopentene-1-carboxylic acid (leucine phenylamide) amide (53 mg, 0.10 mmol) was dissolved in a mixture of tetrahydrofuran (1.9 mL) and 95% ethanol (1.3 mL), and 0.5 N aq. lithium hydroxide (0.65 mL, 0.33 mmol) was added. After being stirred for 24 h at room temperature, the contents of the reaction flask was partitioned between ethyl acetate (30 mL) and 2 N aq. hydrochloric acid (15 mL). The organic layer was washed with saturated aqueous sodium chloride (15 mL), dried over anhydrous sodium sulfate, decanted, and evaporated to give 48 mg of crude product. Flash column chromatography on silica gel (4 g) eluting with 20% ethyl acetate/hexane followed (50 mL) followed by 2% acetic acid/20% ethyl acetate/hexane (50 mL) yielded 45 mg (90% yield) of the title compound as a colorless brittle glass.

$^1$H-NMR (400 MHz, CDCl$_3$) indicated a 1:1 mixture of diastereomers: δ9.13 (s, 0.5H), 8.85 (s, 0.5H), 7.76 (d, 0.5H, J=7 Hz), 7.50 (d, 1H, J=7.5 Hz), 7.43 (d, 1H, J=7.5 Hz), 7.26 (t, 1H, J=7.5 Hz), 7.21 (t, 1H, J=7.5 Hz), 7.12–6.97 (m, 5.5H), 6.85 (s, 0.5H), 4.90 (q, 0.5H, J=7 Hz), 4.81 (q, 0.5H, J=7 Hz), 2.86–1.53 (m, 15H), 1.00 (d, 1.5H, J=6 Hz), 0.98–0.94 (m, 4.5H), 0.93 (t, 1.5H, J=7 Hz), 0.91 (t, 1.5H, J=7 Hz).

EXAMPLE 3

1-(2-(4-Propylphenyl)ethyl)cyclohexane-1,3-dicarboxylic acid 1-(leucine phenylamide) amide Step A:

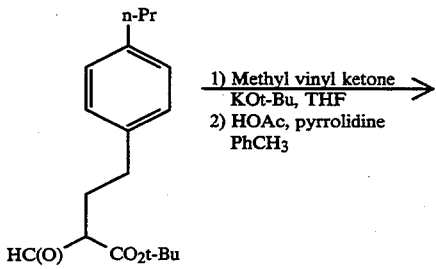

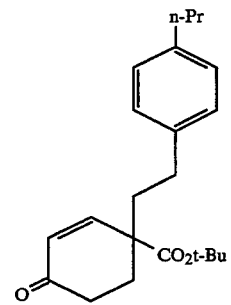

tert-Butyl 1-(2-(4-propyiphenyl)ethyl)-2-cyclohexen-4-one-1-carboxylate. Potassium tert-butoxide (12 mg, 0.11 mmol) was added to a solution of tert-butyl 2-formyl-4-(4-propylphenyl)butanoate (628 mg, 2.16 mmol) in 2.0 mL of tert-butanol. The solution was stirred at 25° C. as methyl vinyl ketone (0.210 mL, 177 mg, 2.52 retool) was added in portions over a 1 hr period. The mixture was stirred 1.5 h longer before being diluted with ethyl acetate (50 mL) and washed with 0.1N aq. hydrochloric acid (20 mL) followed by saturated aq. sodium chloride (20 mL). The organic layer was dried anhydrous sodium sulfate, decanted, and evaporated to give 763 mg of crude intermediate product.

Molecular sieve pellets (4 Å, 0.64 g) were added to a solution of the crude product in toluene (4.0 mL). After addition of pyrrolidine (0.020 mL, 17 mg, 0.24 mmol) and acetic acid (0.040 mL, 42 mg, 0.70 mmol), the reaction was warmed in a 50° C. oil bath for 45 min. The mixture was cooled to 25° C. and diluted with ethyl acetate (40 mL). After washing with 2 N aq. hydrochloric acid (15 mL), saturated aq. sodium bicarbonate (15 mL), and saturated aq. sodium chloride (15 mL), the solution was dried over anhydrous sodium sulfate, decanted, and evaporated. Flash column chromatography on silica gel (25 g), eluting with 800 mL of 7% ethyl acetate/hexane gave 522 mg (71% yield) of the title compound as a colorless oil.

$^1$H-NMR (400 MHz, CDCl$_3$): δ7.11 (d, 2H, J=8 Hz), 7.07 (d, 2H, J=8 Hz), 6.95 (d, 1H, J=10 Hz), 6.00 (d, 1H, J=10 Hz), 2.65–2.42 (m, 6H), 2.11–1.92 (m, 4H), 1.62 sextet, 2H, J=7 Hz), 1.50 (s, 9H), 0.93 (t, 3H, J=7 Hz).

Step B:

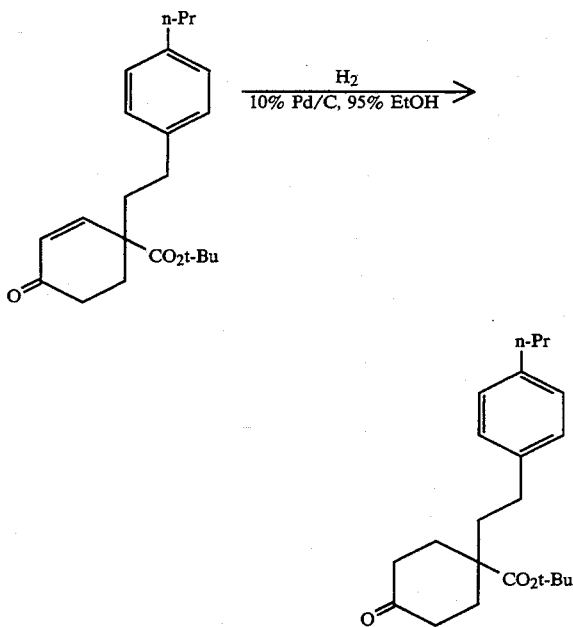

tert-Butyl 1-(2-(4-propylphenyl)ethyl)cyclohexan-4-one-1-carboxylate. A solution of tert-butyl 1-(2-(4-propylphenyl)ethyl)2-cyclohexen-4-one-1-carboxylate (519 mg, 1.52mmol) in 95% ethanol (13 mL) was stirred with 10% Pd/C (50 mg) at room temperature in a round bottom flask connected to a hydrogen-filled balloon. After 6 h, the mixture was centrifuged. The supernatant was filtered through a 0.45 micron membrane and the catalyst was rinsed with additional 95% ethanol. Evaporation of the filtrate gave the title compound in quantitative yield.

$^1$H-NMR (400 MHz, CDCl$_3$): δ7.11 (d, 2H, J=8 Hz), 7.06 (d, 2H, J=8 Hz), 2.58–2.42 (m, 8H), 2.38–2.30 (m, 2H), 1.88–1.82 (m, 2H), 1.70–1.57 (m, 4H), 1.53 (s, 9H), 0.93 (t, 3H, J=7 Hz).

Step C:

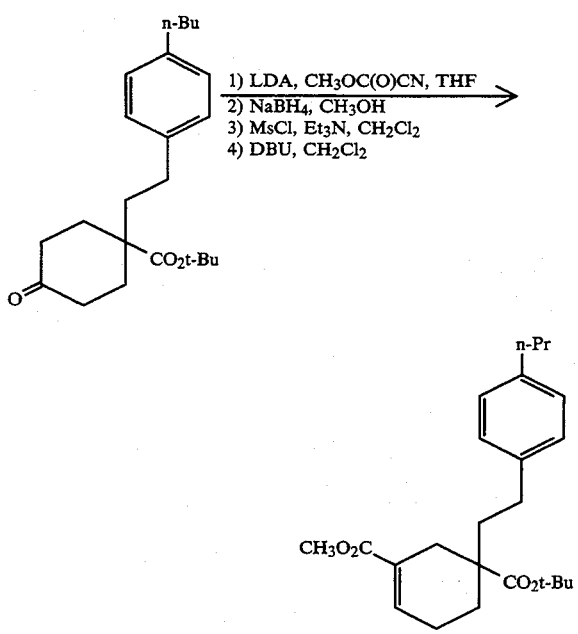

tert-Butyl 3-carbomethoxy-1-(2-(4-propylphenyl)ethyl)-3-cyclohexene-1-carboxylate. A cyclohexane solution of lithium diisopropylamide mono(tetrahydrofuran) complex (0.54 mL, 1.5 M, 0.81 mmol) was added to tetrahydrofuran (4.0 mL) at −78° C. A solution of tert-butyt 1-(2-(4-propylphenyl)ethyl)cyclohexan-4-one-1-carboxylate (250 mg, 0.73 mmol) in tetrahydrofuran (0.40 mL) was added over 5 min, with additional tetrahydrofuran (0.20 mL) to rinse. After 45 min, 1,3-dimethyl-3,4,5,6-tetrahydro-2(1-H)-pyrimidinone (0.10 mL) was added, followed 3 min later by methyl cyanoformate (0.070 mL. 75 mg, 0.88 mmol). The reaction mixture was stirred for 15 min at −78° C. and then quenched by the addition of 1 N aq. hydrochloric acid (10 mL). The mixture was partitioned between ethyl acetate (80 mL) and additional 1 N aq. hydrochloric acid (30 mL). The ethyl acetate layer was washed with saturated aq. sodium chloride (40 mL), dried over anhydrous sodium sulfate, decanted, and evaporated to give 0.36 g of yellow oil. Flash column chromatography on silica gel (10 g), eluting with 600 mL of 4% EtOAc gave 0.24 g of partially purified ketodiester intermediate.

The ketodiester (333 mg, 0.827 mmol) was dissolved in methanol (30 mL) and cooled to 0° C. Sodium borohydride (165 mg, 4.36 mmol) was added and the solution was stirred for 50 min before the addition of acetic acid (1.0 mL). After 10 min, most of the methanol was removed on a rotary evaporator and the residue was diluted with ethyl acetate (50 mL) and washed with 1 N aq. hydrochloric acid (50 mL), saturated aq. sodium bicarbonate (25 mL), and saturated aq. sodium chloride (25 mL). The organic solution was dried over anhydrous sodium sulfate, decanted, and evaporated to yield the crude hydroxydiester as 355 mg of colorless oil.

All of the crude hydroxydiester from the above step was dried by repeatedly dissolving in toluene (6 mL) and evaporating the solution. The residue was dissolved in dichloromethane (15 mL) and triethylamine (0.36 mL, 0.26 g, 2.6 mmol) was added. The solution was cooled to 0° C. and methanesulfonyl chloride (0.095 mL, 140 mg, 1.2 mmol) was added in portions over 45 min. After an additional 2 h at 0° C., the solution was diluted with ethyl acetate (35 mL) and washed with 2 N aq. hydrochloric acid (30 mL). The organic layer was partitioned with additional ethyl acetate (20 mL) and a mixture of saturated aq. sodium bicarbonate (30 mL) and saturated aq. sodium chloride (30 mL). The organic layer was washed with additional saturated aq. sodium chloride (2×20 mL), dried over anhydrous sodium sulfate, filtered, and evaporated to give the crude mesylate as 410 mg of colorless oil.

All of the crude mesylate from the above step was dried by repeatedly dissolving in toluene and evaporating the solution. The residue was dissolved in dichloromethane (55 mL) stirred at room temperature as 1,8-diazabicyclo[5.4.0]undec-7-ene (5.0 mL, 5.1 g, 33 mmol) was added. After 11 h, the solution was washed with 1 N aq. hydrochloric acid (50 mL), saturated aq. sodium bicarbonate (25 mL), and saturated aq. sodium chloride (25 mL). The aqueous layers were extracted successively with dichloromethane (3×30 mL). The organic layers were combined, dried over anhydrous sodium sulfate, decanted, and evaporated. The residue was purified by flash column chromatography on silica gel (40 g), eluting with 750 mL of 4% ethyl acetate/hexane to give the title compound as 114 mg (29% overall yield) of colorless oil.

$^1$H-NMR (400 MHz, CDCl$_3$): δ7.10 (d, 2H, J=8 Hz), 7.07 (d, 2H, J=8 Hz), 6.98-6.94 (m, 1H), 3.75 (s, 3H), 2.91 (d, 1H, J=17 Hz), 2.62 (td, 1H, J=12.5, 4.5 Hz), 2.55 (t, 2H, J=7 Hz), 2.49 (td, 1H, J=12.5, 4.5 Hz), 2.30-2.23 (m, 2H), 2.12 (dd, 1H, J=17, 2 Hz), 2.00 (dt, 1H, J=13, 5 Hz), 1.91 (td, 1H, J=12.5, 4.5 Hz), 1.76 (td, 1H, J=12.5, 4.5 Hz), 1.67-1.52 (m, 3H), 1.46 (s, 9H), 0.93 (t, 3H, J=7 Hz).

Step D:

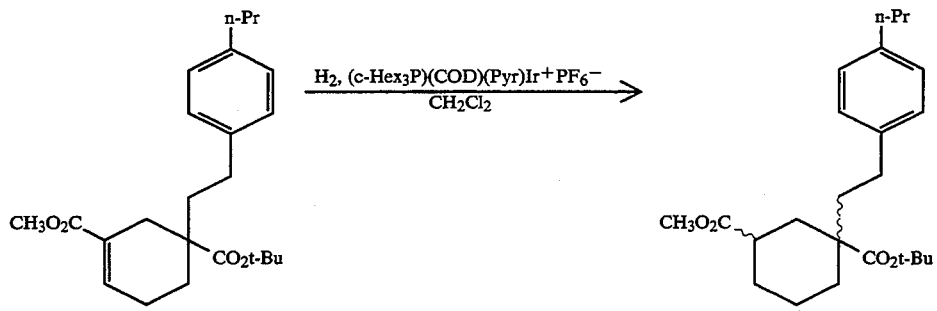

tert-Butyl 3-carbomethoxy-1-(2-(4-propylphenyl)ethyl)-cyclohexane-1-carboxylate. A solution of (tricyclohexylphosphine)(1,5-cyclooctadiene)(pyridine)iridium(I) hexafluorophosphate (47 mg, 0.058 nunol) in dry dichloromethane (0.50 mL) was added to a round bottom flask containing tert-butyl 3-carbomethoxy-1-(2-(4-propylphenyl)ethyl)-3-cyclohexene-1-carboxylate (41 mg, 0.11 mmol) and connected to a hydrogen-filled balloon. After the stirring for 2 h at room temperature, additional catalyst (39 mg, 0.048 mmol) dissolved in dichloromethane (0.40 mL) was added. After another 3 h, the solution was diluted with ethyl acetate (15 mL) and washed with 2 N aq. hydrochloric acid (10 mL), saturated aq. sodium bicarbonate (10 mL), and saturated aq. sodium chloride (10 mL). The solution was dried over anhydrous sodium sulfate, decanted, evaporated, and combined with crude product similarly obtained from 8 mg (0.02 mmol) of the unsaturated ester. Flash column chromatography three times on silica gel (5-8 g) eluting with 3-4% EtOAc/hexane gave 23 mg (47% yield) of the more mobile stereoisomer of the title compound. $^1$HNMR (400 MHz, CDCl$_3$): δ7.09 (d, 2H, J=8 Hz), 7.04 (d, 2H, J=8 Hz), 2.62-2.41 (m, 4 H), 2.54 (t, 2H, J=7 Hz), 2.18 (bd, 1H, J=12 Hz), 1.99-1.93 (m, 1H), 1.80 (td, 1H, J=12.5, 4.5 Hz), 1.76-1.63 (m, 2H), 1.62 (sextet, 2H, J=7 Hz), 1.49 (s, 9H), 1.38-1.29 (m, 2H), 1.24 (t, 1H, J=12 Hz), 1.10 (td, 1H, J=12, 3.5 Hz), 0.93 (t, 3H, J=7 Hz).

Step E:

thoxy-1-(2-(4-propylphenyl)ethyl)cyclohexane-1-carboxylate (23 mg, 0.059 mmol) was dissolved in a mixture of THF (1.15 mL) and methanol (0.75 mL), and 0.5 N aq. lithium hydroxide (0.38 mL, 0.19 mmol) was added. After being stirred for 9 h at room temperature, the contents of the reaction flask was partitioned between ethyl acetate (20 mL) and 2 N aq. hydrochloric acid (10 mL). The organic layer was washed with saturated aqueous sodium chloride (10 mL), dried over anhydrous sodium sulfate, decanted, and evaporated to give 24 mg of crude product.

The crude carboxylic acid was dissolved in a dichloromethane solution (0.25 mL) containing benzyl alcohol (0.012 mL, 13 mg, 0.12 mmol) and 4-(dimethylaminno)-pyridine (1.5 mg, 0.012 mmol). A solution of 1,3-dicyclohexylcarbodiimide (16 mg, 0.078 mmol) in dichloromethane (0.10 mL) was added. After 20 min., an additional portion of dichloromethane (0.10 mL) was added and the mixture was stirred 11 h at room temperature. Hexane (1.5 mL) and water (1 drop) were added. After 20 min., sodium sulfate was added and the mixture was filtered through a cotton plug with additional hexane (3×1.5 mL) to rinse. The flitrate was dried sodium sulfate, decanted, and evaporated. The crude product (36 mg) was purified by chromatography on a silica gel preparative thin layer chromatographic plate (20×20×0.2 cm) eluting with 4% ethyl acetate/hexane to give 22 mg (81% yield) of the title compound as a colorless oil.

$^1$H-NMR (400 MHz, CDCl$_3$): δ7.39-7.30 (m, 5H), 7.09 (d, 2H, J=8 Hz), 7.40 (d, 2H, J=8 Hz), 5.14 (d, 1H, J=12 Hz), 5.10 d, 1H, J=12 Hz), 2.64-2.41 (m, 6H), 2.54 (t, 2H, J=7 Hz), 2.18 (bd, 1H, J=12 Hz), 2.02-1.96 (m, 1H), 1.80 (td, 1H, J=12.5, 4.5 Hz), 1.76-1.65 (m, 2H), 1.62 sextet, 2H, J=7 Hz), 1.48 (s, 9H), 1.39-1.30 (m, 2H), 1.27 (t, 1H, J=12 Hz), 1.10 (td, 1H, J=12, 3.5 Hz), 0.93 (t, 3H, J=7 Hz).

Step F:

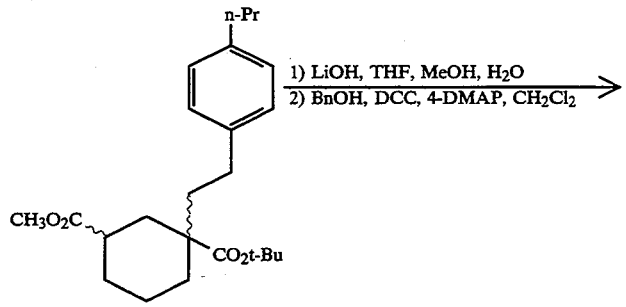

tert-Butyl 3-carbobenzyloxy-1-(2-(4-propylphenyl)ethyl)-cyclohexane-1-carboxylate. tert-Butyl 3-carbome-

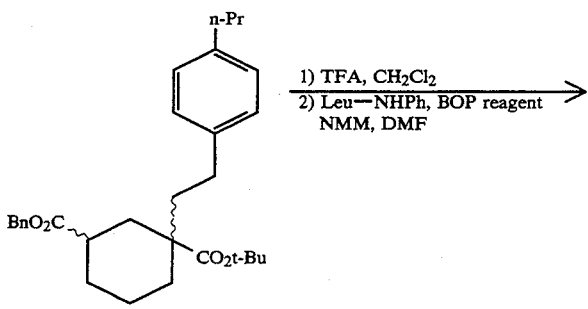 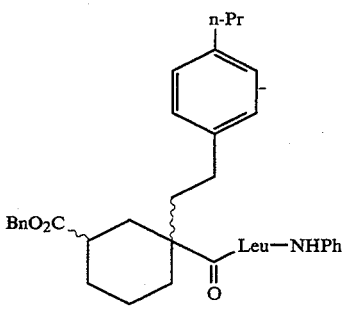

3-Carbobenzyioxy-1-(2-(4-propylphenyl)ethyl)cyclohexane-1-carboxylic acid (leucine phenylamide) amide. Trifluoroacetic acid (2.0 mL, 3.0 g, 26 mmol) was added to a stirred 0° C. solution of 22 mg (0.047 mmol) of tert-butyl 3-carbobenzyloxy-1-(2-(4-propyl-phenyl)ethyl)cyclohexane-1-carboxylate in dichloromethane (2.0 mL). After 2.5 h, toluene (5.0 mL) was added and the solution was evaporated to give crude carboxylic acid as 20 mg of colorless film.

The crude carboxylic acid was dried by evaporation of a toluene solution and then dissolved in dimethylformamide (0.17 mL). Molecular sieves (4 Å, 68 mg) and N-methylmorpholine (0.012 mL, 11 mg, 0.11 mmol) were added. Benzotriazol-1-yloxytris(dimethylamino)phosphonium hexafluorophosphate (26 mg, 0.059 mmol) was added and the solution was stirred for 40 min. before the addition of L-leucine anilide (12 mg, 0.058 mmol). After 1.5 h at room temperature, the solution was diluted with 15 mL of ethyl acetate and washed with 2 N aq. hydrochloric acid (5 mL), saturated aq. sodium bicarbonate (5 mL), and saturated aq. sodium chloride (5 mL). The organic layer was dried over anhydrous sodium sulfate, decanted, and evaporated to give 35 mg of colorless film. Purification by flash column chromatography on silica gel (5 g) packed in dichloromethane, eluting with 100 mL of 1.5% ethyl acetate/dichloromethane gave 22 mg (79% yield) of the title compound as a colorless film.

$^1$H-NMR (400 MHz, CDCl$_3$) indicated a 1:1 mixture of diastereomers: δ8.42 (s, 0.5H), 8.36 (s, 0.5H), 7.52–7.46 (m, 2H), 7.40–7.30 (m, 5H), 7.29–7.23 (m, 2H), 7.07 (t, 1H, J=7 Hz), 7.02 (d, 1H, J=8 Hz), 6.98 (d, 1H, J=8 Hz). 6.92 (d, 1H, J=8 Hz), 6.85 (d, 1H, J=8 Hz), 6.15 (d, 0.5H, J=7 Hz), 6.11 (d, 0.5H, J=7 Hz), 5.14 (d, 0.5H, J=12 Hz), 5.11 (s, 1H), 5.09 (d, 0.5H, J=12 Hz), 4.70–4.61 (m, 1H), 2.62–2.32 (m, 6H), 2.14 (bd, 0.5H, J=12 Hz), 2.08–1.99 (m, 1H), 1.99–1.92 (m, 0.5H), 1.84–1.52 (m, 8H), 1.43–1.22 (m, 4H), 0.99 (d, 1.5H, J=6 Hz), 0.98–0.94 (m, 4.5H), 0.92 (t, 1.5H, J=7 Hz), 0.91 (t, 1.5H, J=7 Hz).

Step G:

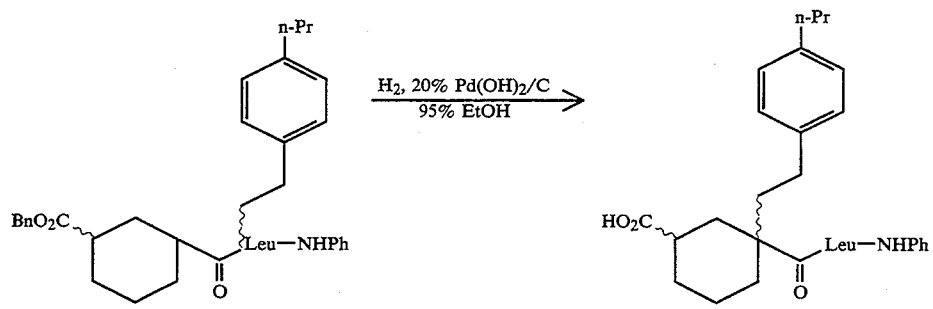

1-(2-(4-Propylphenyl)ethyl)cyclohexane-1,3-dicarboxylic acid 1-(leucine phenylamide) amide. Catalyst (3.5 mg of 20% Pd(OH)$_2$/C.) was added to a solution of 3-carbobenzyloxy-1-(2-(4-propylphenyl)ethyl)cyclohexane-1-carboxylic acid (leucine phenylamide) amide (22 mg, 0.037 mmol) in 95% ethanol (1.5 mL) and the mixture was stirred at room temperature for 2.5 h in a flask connected to a hydrogen-filled balloon. The mixture was centrifuged and the supernatant was filtered through a 0.45 micron membrane. The catalyst was rinsed with additional 95% ethanol and the combined flitrate was evaporated to give 18 mg (96% yield) of the title compound as a colorless glass.

$^1$H-NMR (400 MHz, CDCl$_3$) indicated a 1:1 mixture of diastereomers: δ8.78 (s, 0.5H), 8.62 (s, 0.5H), 7.52 (d, 1H, J=7 Hz), 7.50 (d, 1H, J=7 Hz), 7.43 (bs, 0.5H), 7.29 (t, 1H, J=7 Hz), 7.27 (t, 1H, J=7 Hz), 7.10 (t, 1H, J=7 Hz), 7.04 (d, 1H, J=8 Hz), 6.99 (t, 2H, J=7 Hz), 6.90 (d, 1H, J=8 Hz), 6.73 (d, 0.5 Hz), 4.83–4.74 (m, 1H), 2.64–2.30 (m, 6H), 2.19 (d, 0.5H, J=12 Hz), 2.09–1.97 (m, 1H), 1.85–1.54 (m, 8.5H), 1.46–1.18 (m, 3.5H), 1.08 (bt, 0.5H, J=12 Hz), 0.99 (d, 1.5 H, J=6 Hz), 0.97 (d, 3H, J=6 Hz), 0.96 (d, 1.5H, J=6 Hz), 0.92 (t, 1H, J=7 Hz), 0.91 (t, 1H, J=7 Hz).

EXAMPLE 4

1-(2-(4-Propylphenyl)ethyl)-3-cyclohexene-1,3-dicarboxylic acid 1-(leucine phenylamide) amide Step A:

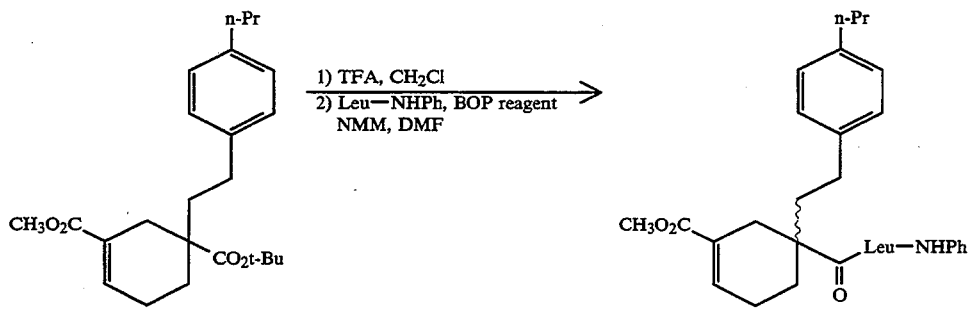

3-Carbomethoxy-1-(2-(4-propylphenyl)ethyl)-3-cyclohexene-1-carboxylic acid (leucine phenylamide) amide. Trifluoroacetic acid (2.0 mL, 3.0 g, 26 mmol) was added to a stirred 0° C. solution of 23 mg (0.060 mmol) of tert-butyl 3-carbomethoxy-1-(2-(4-propylphenyl)-ethyl)-3-cyclohexene- 1-carboxylate in dichloromethane (2.5 mL). After 3 h, toluene (2.0 mL) was added and the solution was evaporated to give crude carboxylic acid as 21 mg of colorless film.

The crude carboxylic acid was dried by evaporation of a toluene solution and then dissolved in dimethylformamide (0.23 mL). Molecular sieves (4 Å, 0.10 g) and N-methylmorpholine (0.015 mL, 14 mg, 0.14 mmol) were added. After 10 min., benzotriazol-1-yloxytris-(dimethylamino)phosphonium hexafluorophosphate (34 mg, 0.077 mmol) was added and the solution was stirred for 40 min. before the addition of L-leucine anilide (16 mg, 0.078 mmol). After 2 h at room temperature, the solution was diluted with 20 mL of ethyl acetate and washed with 2 N aq. hydrochloric acid (10 mL), saturated aq. sodium bicarbonate (10 mL), and saturated aq. sodium chloride (10 mL). The organic layer was dried over anhydrous sodium sulfate, decanted, and evaporated. Chromatography on a silica gel preparative thin layer chromatographic plate (20×20×0.2 cm) eluting with 10% ethyl acetate/toluene gave 26 mg (84% yield) of the title compound as a colorless film.

$^1$H-NMR (400 MHz, CDCl$_3$) indicated a 1:1 mixture of diastereomers: δ8.58 (s, 0.5H), 8.50 (s, 0.5H), 7.47 (d, 2H, J=8 Hz), 7.27 (t, 1H, J=8 Hz), 7.26 (t, 1H, J=8 Hz), 7.11–6.87 (m, 6H), 6.16 (d, 0.5H, J=7 Hz), 6.14 (d, 0.5H, J=7 Hz), 4.68–4.60 (m, 1H), 3.75 (s, 1.5H), 3.74 (s, 1.5H), 2.89 (d, 0.5H, J=16 Hz), 2.87 (d, 0.5H, J=16 Hz), 2.63–2.22 (m, 7H), 2.08–1.90 (m, 2H), 1.84–1.54 (m, 7H), 0.99 (d, 1.5H, J=6 Hz), 0.97 (d, 1.5H, J=6 Hz), 0.96 (d, 1.5H, J=6 Hz), 0.93 (t, 1.5H, J=7 Hz), 0.92 (d, 1.5H, J=6 Hz), 0.92 (t, 1.5H, J=7 Hz).

Step B:

1 -(2-(4-Propylphenyl)ethyl)-3-cyclohexene-1,3-dicarboxylic acid 1-(leucine phenylamide) amide. 3-Carbomethoxy-1-(2-(4-propylphenyl)ethyl)-3-cyclohexene-1-carboxylic acid (lettcine phenylamide) amide (26 mg, 0.050 mmol) was dissolved in a mixture of THF (0.95 mL) and methanol (0.65 mL), and 0.5 N aq. lithium hydroxide (0.33 mL, 0.17 mmol) was added. After being stirred for 24 h at room temperature, the contents of the reaction flask was partitioned between ethyl acetate (30 mL) and 2 N aq. hydrochloric acid (15 mL). The organic layer was washed with saturated aqueous sodium chloride (15 mL), dried over sodium sulfate, decanted, and evaporated to give 26 mg of crude product. Flash column chromatography on silica gel (3 g) eluting with 20% ethyl acetate/hexane followed (50 mL) followed by 2% acetic acid/20% ethyl acetate/hexane (75 mL) yielded 13 mg (52% yield) of the title compound as a colorless film.

$^1$H-NMR (400 MHz, CDCl$_3$) indicated a 1:1 mixture of diastereomers: δ8.95 (s, 0.5H), 8.89 (s, 0.5H), 7.70 (d, 0.5H, J=7 Hz), 7.66 (d, 0.5H, J=7 Hz), 7.52 (d, 1H, J=7.5 Hz), 7.47 (d, 1H, J=7.5 Hz), 7.25 (t, 2H, J=7 Hz), 7.52–7.00 (m, 4H), 6.88 (d, 1H, J=7 Hz), 6.72 (d, 1H, J=7 Hz), 4.87–4.76 (m, 1H), 2.88–2.14 (m, 8H), 2.04–1.50 (m, 9H), 0.97 (d, 3H, J=6 Hz), 0.95 (d, 3H, J=6 Hz), 0.93 (t, 1.5H, J=7 Hz), 0.90 (t, 1.5H, J=7 Hz).

EXAMPLE 5

Enzyme Inhibition Assays

Inhibition of Human Fibroblast Stromelysin:

Activation: Human recombinant stromelysin was purchased from Celltech (Slough, U.K.) as a proenzyme of 55 kD in a buffer consisting of 20 mM Tris, 10 mM CaCl$_2$, 0.05% Brij-35, and 0.2% NAN$_3$, pH=7.5. The material was activated as described. (Harrison, R. K., Teahan, J., and Stein, R. L. A Semi-Continuous HPLC-Based Assay for Stromelysin. Anal. Biochem. 1989, 180, 110–113). Briefly, to 1.0 mL of a 2.2 µM solution of prostromelysin was added 20 µL of a 1.0 µM solution

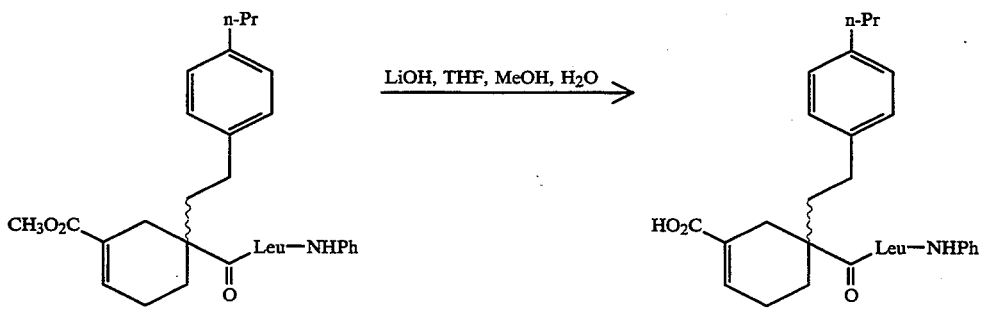

of trypsin in assay buffer (20 mM HEPES, 10 mM CaCl$_2$, 0.05% Brij-35, pH=7.5, [trypsin]$_{final}$=20 nM. The solution was incubated at 37° C. for 30 minutes. The reaction was quenched by addition of a 50 fold molar excess of soybean trypsin inhibitor bound to agarose (Sigma), and the solution centfifuged to remove the trypsin:inhibitor complex.

K$_i$ Determinations: Stock solutions of inhibitors were prepared by dissolving the compounds in DMSO. The inhibitors were further diluted in assay buffer to eight different concentrations encompassing the approximate K$_i$, and coveting a 200 fold range. To 50 μL of each of the inhibitor solutions was added 25 μL of an 8 nM solution of trypsin-activated stromelysin, [DMSO]=1.8%. The solution was allowed to incubate for 4 h to reach equilibrium. To this solution was added 60 μL of a 12.8 μM solution of the substrate Arg-Pro-Lys-Pro-Leu-Ala-Phe-Trp-NH$_2$ (k$_c$/K$_m$=12,000 M$^{-1}$s$^{-1}$) (Niedzwiecki, L., Teahan, J., Harrison, R. K., Stein, R. L. Substrate Specificity of the Human Metalloproteinase Stromelysin and the Development of Continuous, Fluorometric Assays. *Biochem.* 1992, 31, 12618–12623), and the reaction was allowed to proceed for 18 h. In the reaction [S]=5.7 μM and [E]=1.5 nM. The reaction was quenched by addition of 50 μL of 0.15M phosphoric acid, and 100 μL of the reaction mixture was injected onto the HPLC. Since the reactions were run under first order conditions, ([S]<<K$_m$, K$_m$=0.5 mM), the pseudo first order rate constant, k$_{obs}$, was determined for each of the inhibitor concentrations from the peak area corresponding to unreacted substrate in the inhibited sample, and the peak area for substrate at time=0:

$$\ln\left(\frac{\text{area}_{inhib}}{\text{area}_{t=0}}\right) = -k_{obs}t$$

Values of K$_i$ were determined from the ratio of the rate constants for inhibited and control sample (no inhibitor) plotted as a function of the inhibitor concentration, and fit to the following equation:

$$\frac{k_{inhib}}{k_{control}} = \frac{1}{1 + ([I]/K_i)}$$

Inhibition of Human Fibroblast Collagenase:

Activation: Human fibroblast collagenase was purchased from Celltech (Slough, U.K.). The material was received as a proenzyme of 54 kD at a concentration of 1.2 μM in a buffer consisting of 20 mM Tris, 5 mM CaCl$_2$, 0.15 M NaCl and 0.01% NAN$_3$. The material was activated with trypsin using the same procedure as for stromelysin, with the addition that the activation buffer contained 40 nM prostromelysin.

Ki Determinations. Stock solutions of inhibitors were prepared by dissolving the material in DMSO. The inhibitors were further diluted in assay buffer to eight different concentrations encompassing the approximate K$_i$ and covering a 200 fold range. Final DMSO concentration was 2.8%. To 50 uL of the inhibitor solutions was added 25 uL of a 108 nM solution of trypsin activated collagenase. The solution was allowed to incubated for 4 h to reach equilibrium. To this solution was added 60 uL of a 56 μM solution of the substrate DNP-Pro-Leu-Gly-Leu-Trp-Ala-dArg-NH$_2$ (kc/Km=270,000 M$^{-1}$s$^{-1}$) (Stack, M. S.; Gray, R. D. Comparison of Vertebrate Collagenase and Gelatinase Using a New Fluorogenic Substrate Peptide. *J. Biol. Chem.* 1989, 264, 4277–4281), and the reaction was allowed to proceed for 18 h. In the incubation mixture [S]=25 μM, [E]=20 nM. The reaction was quenched by addition of 50 uL of 0.15M phosphoric acid. The reaction mixture was rejected onto the HPLC. The calculation of K$_i$ was the same as for stromelysin.

Inhibition of Human Gelatinase A:

Activation: Human 72kD gelatinase was purchased from Celltech (Slough, U.K.) as a proenzyme at a concentration of 1.5 μM in a buffer consisting of 20 mM Tris, 5 mM CaCl$_2$ 150 mM NaCl, 0.01% brij, 0.02% NAN$_3$, pH=7.5. The proenzyme was activated by incubation of 500 μL proenzyme with 50 μL of a 11 mM solution aminophenyl mercufic acetate in NaOH (pH=11) at 25° C. for 120 min.

Ki Determinations. Determination of K$_i$ values for gelatinase A were identical to that of collagenase and stromelysin with the exception that incubation of the enzyme-inhibitor mixture with the substrate was performed for only 2 h. [S]=25 μM, [E]=20 nM.

This invention also relates to a method of treatment for patients (including man and/or mammalian animals raised in the dairy, meat, or fur industries or as pets) suffering from disorders or diseases which can be attributed to stromelysin as previously described, and more specifically, a method of treatment involving the administration of the matrix metalloendoproteinase inhibitors of Formula I as the active constituents.

Accordingly, the compounds of Formula I can be used among other things in the treatment of osteoarthritis and rheumatoid arthritis, and in diseases and indications resulting from the overexpression of these matrix metalloendoproteinases such as found in certain metastatic tumor cell lines.

For the treatment of rheumatoid arthritis, osteoarthritis, and in diseases and indications resulting from the over-expression of matrix metalloendoproteinases such as found in certain metastatic tumor cell lines or other diseases mediated by the matrix metalloendo-proteinases, the compounds of Formula I may be administered orally, topically, parenterally, by inhalation spray or rectally in dosage unit formulations containing conventional nontoxic pharmaceutically acceptable carders, adjuvants and vehicles. The term parenteral as used herein includes subcutaneous injections, intravenous, intramuscular, intrasternal injection or infusion techniques. In addition to the treatment of wann-blooded animals such as mice, rats, horses, cattle, sheep, dogs, cats, etc., the compounds of the invention are effective in the treatment of humans.

The pharmaceutical compositions containing the active ingredient may be in a form.suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropyl-methyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixrare with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of Formula I are employed. (For purposes of this application, topical application shall include mouth washes and gargles.)

Dosage levels of the order of from about 0.05 mg to about 140 mg per kilogram of body weight per day are useful in the treatment of the above indicated conditions (about 2.5 mg to about 7 gms. per patient per day). For example, inflammation may be effectively treated by the administration of from about 0.01 to 50 mg of the compound per kilogram of body weight per day (about 0.5 mg to about 3.5 gins per patient per day).

The amount of active ingredient that may be combined with the carder materials to produce a single dosage form will vary depending upon the host treated and the particular mode of administration. For example, a formulation intended for the oral administration of humans may contain from 0.5 mg to 5 gm of active agent compounded with an appropriate and convenient amount of carder material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following Examples are intended to illustrate the preparation of compounds of Formula I, and as such are not intended to limit the invention as set forth in the claims appended, thereto.

What is claimed is:

1. A Compound of Formula I:

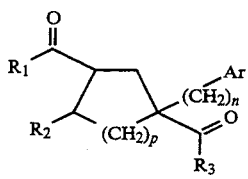

wherein:
n is 1–4;
p is 1–4;
p is 1–2;
Ar is an aryl-group selected from the group consisting of:
 (1) phenyl,
 (2) naphthyl,
which can be mono- or di-substituted with substituents independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, $C_{1-6}$alkylcarbonyl, or unsubstituted or mono- or di-substituted phenyl or naphthyl wherein the substituent is independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, $C_{1-6}$alkylcarbonyl;

$R_1$ is OH, $OC_{1-10}$alkyl, $OCH(C_{1-10}$alkyl$)OC(O)C_{1-10}$alkyl,
OCH$_2$phenyl, wherein the phenyl group may be substituted with hydrogen, carboxy, carboxy$C_{1-3}$alkyl, aminocarbonyl, $C_{1-6}$ alkylaminocarbonyl;

$R_2$ is hydrogen or a mono- or di-substituted $C_{1-6}$alkyl, $C_{1-6}$alkoxy, or $C_{2-6}$alkenyl wherein the substituents are independently selected from the group consisting of:
 (a) hydrogen,
 (b) carboxy,
 (c) aminocarbonyl,
 (d) $C_{1-6}$alkoxy,
 (e) $C_{1-6}$alkylcarbonyl,
 (f) phenyl or naphthyl, which can be substituted as defined above;

$R_3$ is
 (a) mono- or di-substituted $C_{1-10}$alkylamino, or mono- or di substituted di-$C_{1-10}$alkyl amino wherein the substituents are selected from the group consisting of:
  (1) hydrogen,
  (2) mercapto,
  (3) hydroxy,
  (4) carboxy,
  (5) amino,
  (6) aminocarbonyl,
  (7) mono- or di-$C_{1-6}$alkyl amino,
  (8) mono- or di-$C_{1-6}$alkyl aminocarbonyl,
  (9) guanidino,
  (10) phenyl, naphthyl,
 (b) an amino acid derivative of Formula II

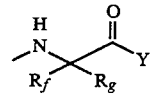

wherein $R_f$ and $R_g$ are individually selected from:
 (a) hydrogen,
 (b) $C_{1-6}$alkyl,
 (c) mercapto $C_{1-6}$alkyl,
 (d) hydroxy $C_{1-6}$alkyl,
 (e) carboxy $C_{1-6}$alkyl,
 (f) amino $C_{1-6}$alkyl
 (g) aminocarbonyl $C_{1-6}$alkyl,
 (h) mono- or di-$C_{1-6}$alkyl amino $C_{1-6}$alkyl,
 (i) guanidino $C_{1-6}$alkyl,
 (j) substituted phenyl $C_{1-6}$alkyl, wherein the substitutent is hydrogen, hydroxy, carboxy, $C_{1-4}$alkyl, or $C_{1-4}$alkyloxy;
and
Y is

wherein $R_6$ and $R_7$ are each individually selected from the group consisting of:
 (a) H,
 (b) $C_{1-10}$alkyl,
 (c) unsubstituted or mono- or disubstituted phenyl or phenyl $C_{1-6}$alkyl wherein the substituent is independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, and $C_{1-6}$alkylcarbonyl.

2. A compound according to claim 1 wherein
Ar is an aryl group which is phenyl, which group can be mono- or di-substituted with the substitutents independently selected from $C_{1-6}$alkyl, halo, hydroxy, $C_{1-6}$alkylcarbonyl, and aryl as defined above in claim 1;

3. A compound according to claim 1 wherein $R_1$ is OH, $OC_{1-6}$alkyl, $OCH_2$phenyl.

4. A compound according to claim 1 wherein $R_2$ is hydrogen or mono- or di-substituted $C_{1-6}$alkyl or $C_{1-6}$alkoxy, wherein the substituents are independently selected from the group consisting of:
 (a) hydrogen,
 (b) $C_{1-6}$alkoxy,
 (c) aryl which is selected from the group consisting of phenyl, which can be mono- or di-substituted with the substitutents independently selected from $C_{1-6}$alkyl, halo, hydroxy, $C_{1-6}$alkylcarbonyl, and aryl as defined above in claim 1;
 (d) aryloxy wherein the aryl groups are defined as in item (c) above;
 (e) aroyl wherein the aryl groups are defined as in item (c) above.

5. A compound according to claim 1 wherein $R_3$ is substituted $C_{1-10}$alkylamino wherein the substituents are selected from the group consisting of:
(1) hydrogen,
(2) aminocarbonyl,
(3) mono- or di-$C_{1-6}$alkyl aminocarbonyl,
(4) aryl wherein the aryl group is selected from the group consisting of:
   (a) phenyl, and
   (b) naphthyl,
which can be mono- or di-substituted with substitutents independently selected from phenyl, $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, and $C_{1-6}$alkylcarbonyl.

6. A compound according to claim 1 wherein $R_3$ is an amino acid derivative of Formula II

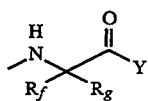

wherein $R_f$ is hydrogen and $R_g$ is selected from:
(a) $C_{1-6}$alkyl,
(b) amino $C_{1-6}$alkyl
(C) aminocarbonyl $C_{1-6}$alkyl,
(d) mono- or di-$C_{1-6}$alkyl amino $C_{1-6}$alkyl,
(e) guanidino $C_{1-6}$alkyl,
(f) substituted phenyl $C_{2-6}$alkyl, wherein the substitutent is hydrogen, hydroxy, carboxy, $C_{1-4}$ alkyl, or $C_{1-4}$alkyloxy.

7. A compound according to claim 6 wherein Formula II is an amino acid selected from alanine, valine, leucine, isoleucine, αtert-butyl glycine, norleucine, serine, threonine, asparagine, glutamine, lysine, homohistidine, arginine, homophenylalanine, homotyrosine, methionine, ornithine, homoserine, and citrulline.

8. A compound according to claim 6 wherein Y is

wherein $R_6$ is hydrogen and $R_7$ is selected from the group consisting of:
(a) $C_{1-10}$alkyl,
(b) unsubstituted or mono- or disubstituted phenyl or phenyl $C_{1-6}$alkyl wherein the substituent is independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, and $C_{1-6}$alkylcarbonyl.

9. A compound according to claim 1 wherein Ar is 4-propylphenyl or 4-biphenyl.

10. A compound according to claim 1 of the Formula:

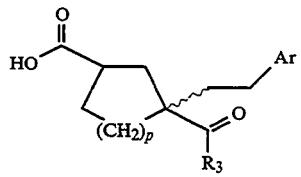

wherein:
p is 1–2;
Ar is 4-propylphenyl or 4-biphenyl;
$R_3$ is an amino derivative of Formula II, as recited in claim 1 wherein said amino acid is selected from alanine, valine, leucine, isoleucine, norleucine, α-tert-butyl glycine, serine, threonine, asparagine, glutamine, lysine, homohistidine, arginine, homophenylalanine, homotyrosine, methionine, ornithine, homoserine, or citrulline; wherein said Y in Formula II is NH-Phenyl.

11. A compound according to claim 10 which is:
(a) 1-(2-(4-Propylphenyl)ethyl)cyclopentane-1,3-dicarboxylic acid 1-(L-leucine N-phenylamide) amide, or
(b) 1-(2-(4-Propylphenyl)ethyl)cyclohexane-1,3-dicarboxylic acid 1-(L-leucine N-phenylamide) amide.

12. A pharmaceutical composition comprising a pharmaceutical carrier and a therapeutically effective amount of a compound according to claim 1.

13. A pharmaceutical composition comprising a pharmaceutical carrier and a therapeutically effective amount of a compound according to claim 11.

* * * * *